(12) United States Patent
Seredenin et al.

(10) Patent No.: US 6,376,666 B1
(45) Date of Patent: *Apr. 23, 2002

(54) 2-MERCAPTOBENZIMIDAZOLE DERIVATIVES POSSESSING PHARMACOLOGICAL ACTIVITY

(75) Inventors: Sergei Borisovich Seredenin; Jury Alexeevich Blednov; Vladimir Leonidovich Saveliev; Tatyana Yakovlevna Mozhaeva; Eleonora Konstantinovna Orlova, all of Moscow; Khagani Sabir Ogly Ragimov, Baku; Milada Alnordovna Yarkova, Moscow; Gennady Georgievich Chichkanov, poselok Junost; Natalia Veniaminova Kaverina, Moscow; Iosif Borisovich Tsorin, Moscow; Galina Jurievna Kirsanova, Moscow; Grigory Georgievich Neznamov, Moscow, all of (RU)

(73) Assignee: Nauchno-Issledovatelsky Institut Farmakologii Rossiiskoi Akademii Meditsinskikh Nauk, Moscow (RU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,369
(22) PCT Filed: May 11, 1995
(86) PCT No.: PCT/RU95/00085
§ 371 Date: Dec. 9, 1996
§ 102(e) Date: Dec. 9, 1996
(87) PCT Pub. No.: WO95/34304
PCT Pub. Date: Dec. 21, 1995

(30) Foreign Application Priority Data

Jun. 10, 1994 (RU) .......................... 94022663
Apr. 18, 1995 (RU) .......................... 95106120

(51) Int. Cl.⁷ ............... $C07D\ 413/06$; $C07D\ 403/06$; $C07D\ 401/06$; $C07D\ 235/28$
(52) U.S. Cl. ............ 544/139; 544/370; 546/199; 548/307.1
(58) Field of Search ............ 548/307.1; 514/395; 544/139, 370; 546/199

(56) References Cited

U.S. PATENT DOCUMENTS 4,045,564 A    8/1977   Berntsson et al. .......... 424/263

(List continued on next page.)

FOREIGN PATENT DOCUMENTS

CH    642359    *   4/1984

(List continued on next page.)

OTHER PUBLICATIONS

Johnson et al, "Synthesis of some new leads trypanocidal, etc" CA 117:2512772, 1992.*

(List continued on next page.)

Primary Examiner—Alan L. Rotman
(74) Attorney, Agent, or Firm—Ladas & Parry

(57) ABSTRACT

2-mercaptobenzimidazole derivatives of the general formula

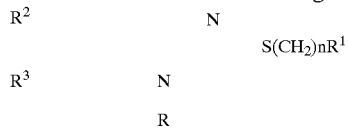

wherein: N=0,2,3; R-hydrogen atom, aralkyls; R1-lower alkyls, alkenyls, dialkylamino, a saturated amine monocyclic residue which may contain an additional heteroatom; $R^2$ and $R^3$ are equal or different and stand for hydrogen atoms, lower alkyls, alkoxy in various positions, and their pharmaceutically acceptable salts, according to the results of pharmacological research study exhibit a pronounced anxiolytic, sedative, antiischemia and antiarrhythmia effect and have certain advantages over popular clinic preparations. These can find a wide variety of application for treatment of patients suffering from various mental derangements and heart ischemia.

4 Claims, 6 Drawing Sheets

U.S. PATENT DOCUMENTS

Figure 1:
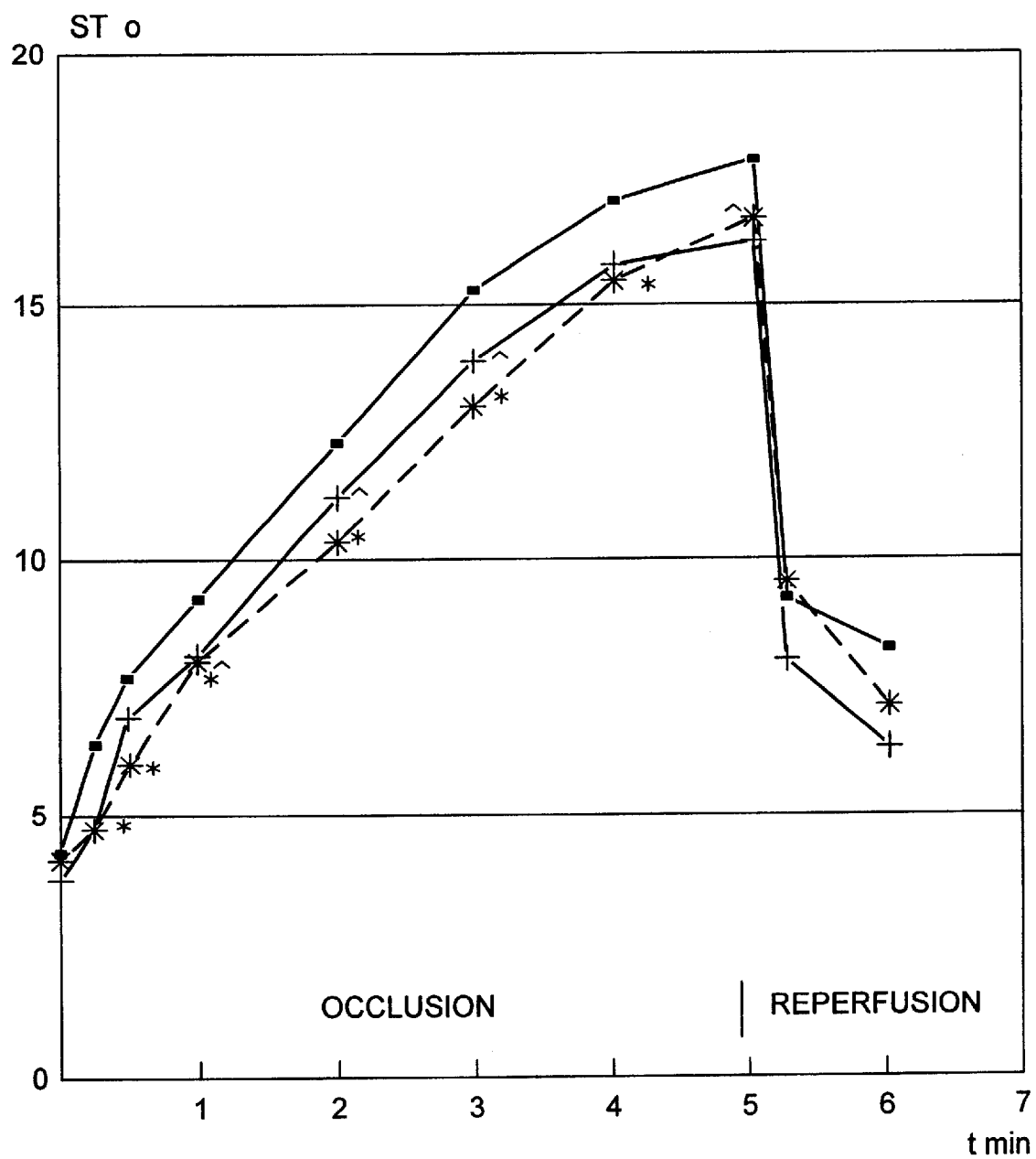

| | | | | |
|---|---|---|---|---|
| 4,746,667 A | | 5/1988 | Carlsson et al. | 514/338 |
| 4,814,329 A | * | 3/1989 | Harsanyi et al. | 514/211 |
| 4,873,346 A | * | 10/1989 | Anderson | 548/157 |
| 4,983,620 A | * | 1/1991 | Giani et al. | 514/395 |
| 5,185,347 A | * | 2/1993 | Katano et al. | 514/322 |
| 5,387,600 A | * | 2/1995 | Aikawa et al. | 514/395 |

FOREIGN PATENT DOCUMENTS

| | | | |
|---|---|---|---|
| EP | 0419210 | | 3/1991 |
| FR | 6283 | * | 9/1968 |
| RU | 2027709 | * | 6/1991 |
| SU | 1502571 | | 8/1989 |

OTHER PUBLICATIONS

Dini et al., "Antihistamisic/antiallergic activity, etc" Agents and aikens, 30, 1/2 pp. 174–177, 1990.*

Krutovskikh, et al, "Radioprotective properties, etc" CA 93:114390, 1980.*

Abramova et al, "Reactions of 1–vinylbenzimidazole, etc" CA 101:230408, 1984.*

Ghoneim et al, "1,2–disubstituted benzimidazoles," CA 112: 138959, 1990.*

Yoshioka, et al I, "Preflux treatment of copper, etc" CA 118:114904, 1993.*

Yoshioka, et al II, "Manufacture of copper–clad through, etc" CA 117:183388, 1992.*

Malkines, et al, "Toxic and radioprotective properties, etc" CA 93:385, 1980.*

Ozawa et al, "Catechol amine biosynthesis. I., etc" CA 75:59008, 1971.*

Laboratories Cassenne II, "Antipyretic 2–mercapto–, etc" CA 72:12729, 1970.*

Yamada et al, "Preparation of 1–(biphenyl yl alkyl), etc" CA 118:147559, 1993.*

Hasegawa, et al "Benzimidazole derivatives" CA 82: 156308K, 1975.*

Seredenin, S. et al. Molecular–Biological Problems of Developing Medicaments and the Study of their Action Mechanism, *The Chemical–Pharmaceutical Journal*, No 2, Moscow 1987, pp 134 to 173, in Russian and English.

Borisovitch, T.I., "The Effect of Anti–Hypoxtant Agents (Sodium Oxybutyrate, Pyracetam, Pyridoxynyl–Glyoxylate) on Experimental Myocardia Ischemia", The Academy of Medical Sciences of the USSR, Moscow, 1985, pp 47 and 48 in Russian and English.

* cited by examiner

2-MERCAPTOBENZIMIDAZOLE DERIVATIVES POSSESSING PHARMACOLOGICAL ACTIVITY

This application is a 371 of PCT/RU95/00085 filed May 17, 1995.

THE FIELD OF TECHNIQUES

The invention relates to new S- and N,S-substituted 2-mercaptobenzimidazoles which can be useful as the pharmaceutical agents and pharmacological compositions including these compounds. The applied compounds are the pharmacologically active drugs which possess psychotropic and cardiovascular actions depending on their structure. They can be used in medicine for treatment of different neuropsychiatric disturbances and ischemic heart disease.

THE PRECEDING LEVEL OF TECHNIQUES

The preparation of numerous substituted 2-mercaptobenzimidazoles possessing different biological activities is known in the literature. The first information about the activity of this series appeared in 1958 when Knobloch W. et al. [Arch.Pharmaz., 1958, 291, p.113–118] and Nakajima S. et al. [Yakugaku Zasshi, 1958, 78, p.1378–1388] described the synthesis of different 2-alkyl-, alkenyl-, aralkyl-, dialkylaminoalkylbenzimidazoles having anti-fungal activity. In the following numerous papers [Nakajima S. et al., Jap.Pat., 10978 ('61), (1961); Hideg K. et al., Brit.Pat., 1234058, (1971); Xin Tao et al., Zhongguo Yiyao Gongye Zazhi, 1990, 21 (8), p.347–350; Johnson C. A. et al., Med.Chem.Rec., 1992, 2 (4), p.247–255; Onkol et al., J.Fac.Pharm.Gazz.Univ., 1992, 9 (1), p.47–57; etc.] there were discribed 2-mercaptobenzimidazoles with different substitutions in S-, N- and benzol ring possessing bacteriostatic, insecticidal and anthelminthic activities.

There was reported about Anti-inflammatory, antipyretic and antidepressant activities of different S-substituted-2-mercaptobenzimidazoles were reported in French Special Medicament Patent. The data about anti-inflammatory and analgetic activities of the 2-mercaptobenzimidazole derivatives are described in papers of Seki et al. [Yakugaku Zasshi, 1962, 82, p.1620–1624], Hasegawa H. et al. [Jap.Pat., 7441198 (1974)], Aka T. et al. [Jap.Pat., 9888 ('64) (1964)], Lafon V. et al. [Ger.Offen 2246429 (1978)], Rao V., Madhusudan et al. [Indian Drugs, 1987, 24 (12), p.545–548], Lazer E. S. et al. [J.Med.Chem., 1987, 30, p.726–729].

The synthesis of 2-dialkylaminoalkylbenzimidazoles substituted in N-atom with anti-histaminic and anti-allergic properties was described by Giani R. et al. [Eur.Pat.Appl. EP334818 (1989)] and Dini S. et al. [Agents Actions, 1990, 30, p.174–177].

There have been patented many different S-substituted-2-mercaptobenzimidazoles with anti-ulcerous activity [Machinami T. et al., Eur.Pat.Appl. EP 452076 (1991); Lang H. J. et al., Eur.Pat.Appl. EP 213474 (1987); Adelstein G. W. et al., Eur.Pat.Appl. EP 204215 (1986); Okitsu M., Jpn. Kokai Tokkyo Koho JP 62230773 (1987); Hirai K. et al., Jpn. Kokai Tokkyo Koho JP 62331158 (1987); Okabe S. et al., Jpn. Kokai Tokkyo Koho JP 03227927 (1991); Riedel R. et al., PCT Int.Appl. WO 87/01114 (1986); Klemm K. et al., PCT Int.Appl. WO 9204898 (1992) etc.]. Some of them—omeprazol, lansoprazol are widely used in clinical practice.

Synthesis of N-substituted-2-alkylthiobenzimidazoles possessing the properties of antagonists of angiotensin II and inhibitors of dopamine-β-hydroxylase was reported in the patents of Hauel et al. [Eur.Pat.Appl. EP 502314 (1992)] and Smithkline Beckman Corp. [Jpn. Kokai Tokkyo Koho JP 61161267 (1986)].

There are known some papers describing the synthesis of some 2-mercaptobenzimidazole derivatives with cardiotonic, vasodilative, anti-hypertensive, anti-atherosclerotic and anti-agglutinate properties [Osawa Y. et al., Yakugaku Zasshi, 1968, 88 (6), p.747–754; Brukshtus A. B. et al., Khimiko-Farmatcevt.Zhurnal, 1992, N 11–12, p.50–53; 1994, N 6, p.24–26; Bru-Magniez N. et al., Eur.Pat.Appl. EP 385850 (1990); Harsanyi K. et al., UK Pat.Appl. GB 217319A (1986)]. There were revealed some compounds with anti-ischemic, anti-arrhythmic and anti-hypoxant activities among synthesized 2-dialkylamino-alkylthiobenzimidazoles [Patent of Russia, 2027709 (1991)].

Some substituted 2-mercaptobenzimidaziles with butyrophenon in the 1st position are characterised by psychotropic properties including the tranquilising and neuroleptic types of activity [Sato Makoto et al., Japan Kokai 7584578 (1975); 76136674 (1976); 76146473 (1976)].

The bemityl-2-ethylbenzimidazole hydrobromide is used in clinical practice as the psychostimulator and antihypoxant for the treatment of asthenic and asthenic-depressant disturbances according to the data of Bobkov Yu. G. et al. [Author Certificate of USSR 1251374 (1986)] and Neznamov G. G. et al. [Physiol.Active Drugs, 1993, 25, p.45–49]. According to Losinskyi M. O. et al. [Author Certificate of USSR 1259652 (1986)] the bemityl's analogue-5-ethoxy-2-ethylthiobenzimidazole produces the stress-protective and antihypoxant activities. Plotnikov E. M. et al. [Physiol.Active Drugs, 1993, 25, p.30–34] and Ratnikov L. I. et al. [Physiol.Active Drugs, 1993, 25, p.27–29] have shown that these compounds may be used for the treatment of acute cerebrovascular disturbances and acute respiratory viral infections.

DISCLOSURE OF THE INVENTION

The compounds of the present invention are derivatives of 2-mercaptobenzimidazole general formula

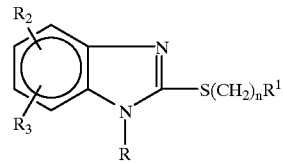

where in n=0,2,3; R-hydrogen atom, aralkyls; $R^1$-lower alkyls, alkenyls, dialkylamino, monocyclic saturated amino group, which can contain additional heteroatom; $R^2$ and $R^3$-identical or different and represent hydrogen atoms. lower alkyls, alkoxy in various positions. These compounds have tranquilising activity with selective component, sedative, anti-ischaemic and anti-arrithmic activity and can be used in medicine.

The applied compounds and their pharmaceutically acceptable salts were synthesized by standard method of alkylation 2-mercaptobenzimidazoles by corresponding agents in ethanol-water medium in the presence of base (sodium hydroxide) with following treatment of obtaining oily or crystalline bases in the solution of absolute ethanol or ether with ethanolic or etherial solution of gaseous hydrogen chloride:

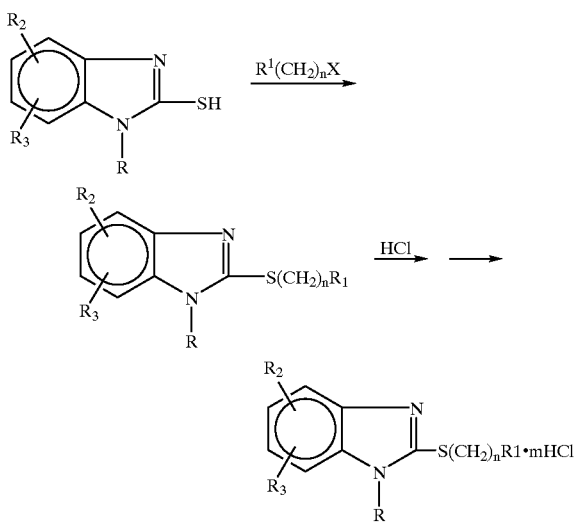

wherein n, R, R$^1$, R$^2$, R$^3$ have foregoing sense; X-atom of chlorine or bromine; m=1,2,3.

Variant of the Realization of the Invention

The reaction processes were controlled by using TLC—Silufol UV 254 or DC-Alufolien Aluminiumoxid 60 F 254 (Merk), spots were detected by uv absorbance or iodine vapor. Melting points were determined in the opened cappilaries and were not corrected. NMR spectra were recorded with AC-250 Bruker using CDCl$_3$ or D$_2$O as solvent and tetramethylsilane as internal reference.

The invention was illustrated by the following examples.

Example 1. 2-Ethylthio-5,6-dimethylbenzimidazole (I). 0,65 g (6 mmol) Ethylbromide was added to a solution 0,89 g (0,005 mol) 2-mercapto-5,6-dimethylbenzimidazole and 0,24 g (0,006 mol) sodium hydroxide in 1 ml of water and 10 ml of ethanol. The reaction mixture was refluxed for 1.5 hr before disappearing starting thione (control by using TLS), cooled and added water. The precipitated product was filtered off, washed with water and dried under atmospheric conditions. The yield was 0,91 g (88%) of compound I, m.p. 123–124° C. (from water-ethanol).$^1$H NMR (CDCl$_3$), δ: 1.37 (3H, t, CH$_2$CH$_3$); 2,32 (6H, s, 2CH$_3$); 3,27 (2H, q, CH$_2$CH$_3$); 7,31 (2H, s, ArH).

Calcd for C$_{11}$H$_{14}$N$_2$S: C 64,0; H 6,8; N 13,61 S 15,5; Found: C 63,9; H 6,8; N 13,4; S 15,5.

Example 2. 2-Propylthio-5,6-dimethylbenzimidazole (II) was prepared by the same procedure for I from 0,89 g (0,005 mol) 2-mercapto-5,6-dimethyl-benzimidazole, 0,8 g (0,006 mol) propylbromide in the presence 0,24 g (0,006 mol) sodium hydroxide in a yield of 0,72 g (60%), m.p. 122–123° C. (from mixture ethylacetate with hexane).

Calcd for C$_{12}$H$_{16}$N$_2$S. C 64,2; H 7,2; N 12,5; S 14,3; Found: C 64,7; H 7,2; N 12,6; S 14,4.

Example 3. 2-Allylthio-5,6-dimethylbenzimidazole (III) was prepared as described above for I from 2,67 g (0,015 mol) 2-mercapto-5,6-dimethyl-benzimidazole, 2,1 g (0,017 mol) allylbromide in the presence 0,7 g (0,017 mol) sodium hydroxide, yield 2,5 g (76%), m.p. 119–120° C. (from mixture ethylacetate with hexane). $^1$H NMR (CDCl$_3$), δ: 2,33 (6H, s, 2CH$_3$); 3,89 (2H, d, CH$_2$S); 5,10 (H$_B$, d, CH$_C$=CH$_A$H$_B$); 5,25 (H$_A$,d, CH$_C$=CH$_A$CH$_B$); 7,30 (2H, broad s, ArH); 10,11 (1H, broad s, NH).

Calcd for C$_{12}$H$_{14}$N$_2$S: N 12,8; S 14,7; Found: N 12,7; S 14,7.

Hydrochloride of base III, yield 93%, m.p. 204–205° C. (with decomp.; from abs. ethanol).

Cacld for C$_{12}$H$_{14}$N$_2$S*HCl. C 56,6; H 5,9; Cl 13,9; N 11,0; S 12,6.

Example 4. 2-Allylthio-5-ethoxybenzimidazole (IV) and its hydrochoride. To a solution 1,95 g (0,010 mol) 2-mercapto-5-ethoxybenzimidazole and 0,44 g (0,011 mol) sodium hydroxide in 2 ml of water and 20 ml of ethanol was added 1,32 g (0,011 mol) allylbromide. The reaction mixture was refluxed for 3 hr, cooled and diluted with water, the forming oil was extracted with ether, dried over anhedrous magnesium sulfate, filtered and the solvent was removed. The compound IV was obtained as an oil, which was disolved in abs. ether and treated with etherial solution of HCl. The precipitate was filtered, washed with abs. ether and dried under atmospheric condition. The yield was 2 g (74%) of hydrochloride of base IV, m.p. 147–149° C. (decomp.; from abs. ethanol with ether). $^1$H NMR (D$_2$O), δ: 1,54 (3H, t, CH$_2$CH$_3$); 4,05 (2H, d, CH$_2$S); 4,18 (2H, q, CH$_2$CH$_3$); 5,34 (H$_B$, d, CH$_C$=CH$_A$H$_B$); 5,42 (H$_A$, d, CH$_C$=CH$_A$CH$_B$); 6,11 (H$_C$, m, CH$_C$=CH$_A$H$_B$); 7,07 (1H, broad s, 4-H); 7,09 (1H, dd, 6-H); 7,53 (1H, d, 7-H).

Calcd for C$_{12}$H$_{14}$N$_2$OS*HCl: C 53,2; H 5,6; Cl 13,1; N 10,3; S 11,8. Found: C 53,4; H 5,6; Cl 13,11 N 10,3; S 11,9.

Example 5. 2-[2-(Dimethylamino)ethylthio]-5-methoxybenzimidazole and its hydrochloride were obtained as described above. The reaction of 3,6 g (0,020 mol) 2-mercapto-5-methoxybenzimidazole, 3,17 g (0,022 mol) 2-(dimethyl-amino)-ethylchloride hydrochloride in the presence 1,8 g (0,044 mol) sodium hydroxide gave V as an oil, from which its dihydrochloride was prepared in a yield of 4,5 g (69%), m.p. 252–254° C. (decomp., from ethanol with charcoal). $^1$H NMR (D$_2$O), δ: 3,07 (6H, s, (CH$_3$)$_2$N); 3,67 (2H, m, CH$_2$S); 3,82 (2H, m, CH$_2$N); 3,96 (3H, s, CH$_3$O); 7,16 (1H, broad s, 4-H), 7,17 (1H, d, J$_{6,7}$9,5,6-H); 7,57 (1H, J$_{7,6}$9,5, 7-H).

Calcd for C$_{12}$H$_{17}$N$_3$OS*2HCl: C 44,4; H 5.9; Cl 21,9; N 13,0; S 9,9. Found: C 44,3; H 5,8; Cl 21,7; N 12,5; S 9,7.

Example 6. 2-2-[(Diethylamino)ethylthio]-5-ethoxybenzo-imidazole (VI) and its dihydrochloride were obtained as described above. The reaction of 3,6 g (0,020 mol) 2-mercapto-5-ethoxybenzimidazole, 4,4 g (0,022 mol) 2-(diethyl-amino)ethyl-chloride hydrochloride gave an oily base VI, from which its hydrochloride was prepared in a yield of 4,4 g (62%), m.p. 209–210° C. (with decomp., from ethanol with charcoal). $^1$H NMR (D$_2$O), δ: 1,37 (6H, t, 2 CH$_2$CH$_3$); 3,40 (4H, q, 2 CH$_2$CH$_3$); 3,63 (2H, m, CH$_2$S); 3,79 (2H, m CH$_2$N); 3,93 (3H, s, CH$_3$O); 7,12 (1H, broad s, 4-H); 7,13 (1H, dd, J$_{4,6}$1,5, J$_{6,7}$9,5, 6-H); 7,56 (1H, d, J$_{7,6}$9,5, 7-H).

Calcd for C$_{14}$H$_{21}$N$_3$OS*2HCl: C 47,7; H 6,6; Cl 20,1; N 11,9; S 9,1; Found C 47,7; H 6,4; Cl 20,3; N 12,2; S 8,5.

Example 7.2-[2-(Piperidino)ethylthio]-5-methoxybenzimidazole (VII) and its dihydrochloride were prepared as described above. The reaction of 2,7 g (0,015 mol) 2-mercapto-5-methoxybenzimidazole and 3,03 g (0,016 mol) 2-(piperidino)ethylchloride hydrochloride in the presence of 1,4 g (0,034 mol) sodium hydroxide gave an oily base VII, from which its hydrochloride was obtained in a yield of 3,15 g (58%), m.p. 210–212° C. (with decomp., from mixture abs. ethanol with ether).

Calcd for C$_{15}$H$_{21}$N$_3$OS*2HCl: C 49,5; H 6,4; Cl 19,5; N 11,5; S 8,8; Found: C 49,6; H 6,2; Cl 19,3; N 11,3; S 9,0.

Example 8. 2-[2-Dimethylamino)ethylthio]-5-ethoxybenzo-imidazole (VIII) and its dihydrochloride were synthesized as described above. The reaction of 1,94 g (0,010 mol) 2-mercapto-5-ethoxybenzimidazole and 1,72 g (0,012 mol) 2-(dimethylamino)ethylchloride hydrochloride in the presence of 0,9 g (0,022 mol) sodium hydroxide gave 1,9 g (72%) compound VIII, m.p. 95–97° C. (from ethanol with water). $^1$H NMR (CDCl$_3$), δ: 1,40 (3H, t, C$\underline{H_3}$CH$_2$O); 2,40 (6H, s, (CH$_3$)$_2$N); 2,84 (2H, t, CH$_2$S); 3,17 (2H, t, CH$_2$N); 4,05 (2H, q, CH$_3$C$\underline{H_2}$O); 6,82 (1H, dd, J$_{4,6}$2,38, J$_{6,7}$8,76, 6-H); 6,94 (1H, broad s, 4-H); 7,36 (1H, d, J$_{7,6}$8 76, 7-H). Dihydrochloride of base VIII, yield 77%, m.p. 223–227° C. (with decomp., from mixture abs. ethanol with ethylacetate).

Calcd for C$_{13}$H$_{19}$N$_3$OS*2HCl: C 46,2; H 6,3; Cl 21,0; N 12,4; S 9,5; Found: C 46,4; H 6,2; Cl 20,7; N 12,2; S 9,6.

Example 9. 2-[2-(Diethylamino)ethylthio]-5-ethoxybenzimidazole (IX) and its dihydrochloride were synthesized as described above. The reaction of 3,9 g (0,020 mol) 2-mercapto-5-ethoxybenzimidazole and 4,4 g (0,022 mol) 2-(diethylamino)-ethylchloride hydrochloride in the presence of 1,8 g (0,044 mol) sodium hydroxide gave an oily base IX, from. which its dihydrochloride was obtained in a yield of 4,4 g (57%), m.p. 169–171° C. (with decomp., from ethanol with ether). $^1$H NMR (D$_2$O), δ: 1,42 (6H, t, (C$\underline{H_3}$CH$_2$)$_2$N); 1,53 (3H, t, CH$_3$CH$_2$O); 3,44 (4H, q, (CH$_3$C$\underline{H_2}$)$_2$N); 3,68 (2H, t, CH$_2$S); 3,82 (2H, t, CH$_2$N); 4,19 (2H, q, CH$_3$C$\underline{H_2}$O); 7,19 (1H, broad s, 4-H); 7,21 (1H, unresolv.d, 6-H); 7,59 (1H, d, J$_{7,6}$9,75, 7-H).

Calcd for C$_{15}$H$_{23}$N$_3$OS*2HCl*H$_2$O: C 46,9; H 7,1; Cl 18,5; N 10,9; S 8,3; Found: C 46,9; H 6,8; Cl 18,6; N 10,6; S 8,0.

Example 10. 2-[2-(Pyrrolidino)ethylthio]-5-ethoxybenzimidazole (X) and its dihydrochloride were sythesized as described above. The reaction of 1,94 g (0,010 mol) 2-mercapto-5-ethoxybenzimnidazole and 2,04 g (0,012 mol) 2-(pyrrolidino)ethylchloride hydrochloride in the presence of 0,9 g (0,022 mol) sodium hydroxide gave X as an oil, which was converted into its dihydrochloride in a yield of 2,7 g (72%), m.p. 127–130° C. (with decomp., from abs. ethanol with ether).

Calcd for C$_{15}$H$_{21}$N$_3$OS*2HCl*0,5H$_2$O: C 48,3; H 6,5; Cl 19,0; N 11,3; S 8,6; Found: C 48,6; H 6,8; Cl 19,0, N 10,9; S 8,7.

Example 11. 2-[2-Piperidino)ethylthio]-5-ethoxybenzimidazole (XI) and its dihydrochloride were synthesized as described above. The reaction of 1,94 g (0,010 mol) 2-mercapto-5-ethoxybenzimidazole and 2,21 g (0,012 mol) 2-(piperidino)ethylchloride hydrochloride in the presence of 0,9 g (0,022 mol) sodium hydroxide gave base XI as an oil, from which its hydrochloride was prepared in a yield of 2,1 g (57%), m.p. 187–190° (with decomp., from mixture abs.ethanol with ethylacetate).

Calcd for C$_{16}$H$_{23}$N$_3$OS*2HCl*0,5H$_2$O: C 49,6; H 6,8; Cl 18,3; N 10,9; S 6,2. Found: C 49,6; H 6,7; Cl 18,5; N 10,8; S 6,0.

Example 12. 2-[2-(Morpholino)ethylthio]-5-ethoxybenzimidazole (XII) and its dihydrochloride were synthesized as described above. The compound XII was obtained as an oil from 2,9 g (0,015 mol) 2-mercapto-5-ethoxybenzimidazole and 3,45 g (0,018 mol) 2-(morpholino)ethylchloride hydrochloride in the presence of 1,35 g (0,033 mol) sodium hydroxide. The oil was disolved in ethylacetate, extracted by 10% solution hydrochloric acid, the layers were separated, the aqueous phase was refluxed with charcoal, was filtered and was made alkaline with the solution of sodium hydroxide. The obtained oil was extracted with ethylacetate, washed with water, dried over anhydrous magnesium sulfate, the solvent was evaporated. The compound XII was obtained in 87% yield (4 g) as an oil. $^1$N NMR (CDCl$_3$), δ: 1,48 (3H, t, CH$_2$C$\underline{H_3}$); 2,59 (4H, m, CH$_2$NCH$_2$ of morpholine); 3,24 (2H, m, CH$_2$N); 3 79 (4H, m CH$_2$OCH$_2$ of morpholine); 4,02 (2H, q, C$\underline{H_2}$CH$_3$); 6,82 (1H, dd, J$_{4,6}$ 2,38, J$_{6,7}$8,77, 6-H); 7,00 (1H, broad s, 4-H); 7,41 (1H, d, J$_{7,6}$8,77, 7-H).

Calcd for C$_{15}$H$_{21}$N$_3$O$_2$S. C 58,6; H 6,9; N 13,7; S 10,4; Found: C 58,6; H 6,8; N 13,9; S 10,1.

Dihydrochloride of compound XII, yield 91%, m.p. 191–192° C. (with decomp., from ethanol with charcoal). $^1$H NMR (D$_2$O), δ: 1,54 (3H, t, OCH$_2$C$\underline{H_3}$); 3,58 (4H, ?m, CH$_2$NCH$_2$ of morpholine); 3,74 (2H, m, CH$_2$S); 3,86 (2H, m, CH$_2$N); 4,12 (4H, unresolv. m, CH$_2$OCH$_2$ of morpholine); 4,25 (2H, q, OC$\underline{H_2}$CH$_3$); 7,21 (1H, d, J$_{6,7}$8,76, 6-H); 7,22 (1H, s, 4-H); 7,41 (1H, d, J$_{7,6}$8,76 7-H).

Calcd for C$_{15}$H$_{21}$N$_3$O$_2$S*2HCl. C 47,4; H 6,1; Cl 18,6; N 11,0; S 8,4; Found: C 47,3; H 6,1; Cl 18,6; N 11,0; S 8,4.

Example 13. 2-[2-(Pyrrolidino)ethylthio]-5,6-dimethylbenzimidazole (XIII) and its dihydrochloride were synthesized as described above. The compound XIII was obtained from 2,67 g (0,015 mol) 2-mercapto-5,6-dimethylbenzimidazole and 2,9 g (0,017 mol) 2-(pyrrolidino)ethylchloridehydrochloride in the presence 1,35 g (0,034 mol) sodium hydroxide in 90% yield (4,0 g, counting on monohydrate), m.p. 115–116° C. (with decomp., from ethanol with water). $^1$H NMR (CDCl$_3$), δ: 1,97 (4H, m, β-H of pyrrolidine); 2,34 (6H, s, 2CH$_3$); 2,72 (4H, m, ɜ-H of pyrrolidine); 3,02 (2H, m, CH$_2$S); 3,19 (2H, m, CH$_2$N); 7,18 (2H, broad s, ArH).

Calcd for C$_{15}$H$_{21}$N$_3$S*H$_2$O: C 61,4; H 7,8; N 14,3; S 10,9; Found: C 61,4; H 7,8; N 14,5; S 10,9.

Dihydrochloride of XIII, quantitative yield, decomp.p. 240° C. (from abs.ethanol with ethylacetate).

Calcd for C$_{15}$H$_{21}$N$_3$S*2HCl: C 51,7; H 6,7; Cl 20,4; N 12,1; Found: C 51,7; H 6,5; Cl 20,4; N 12,1.

Example 14. 2-[2-(Piperidino)ethylthio]-5,6-dimethylbenzimidazole (XIV) and its dihydrochloride were synthesized as described above. The reaction of 2,67 g (0,015 mol) 2-mercapto-5,6-dimethylbenzimidazole with 3,13 g (0,017 mol) 2-(piperidino)ethylchloride hydrochloride in the presence of 1,36 g (0,034 mol) sodium hydroxide gave in 93% yield (counting on monohydrate) 4,3 g of compound XIV, m.p. 117–119° C. (with decomp., from ethanol with water). $^1$H NMR (CDCl$_3$), δ:1,65 (2H, broad m, γ-H of piperidine); 1,82 (4H, m, β-H of piperidine); 2,34 (6H, s, 2CH$_3$); 2,63 (4H, broad m, α-H of piperidine); 2,90 (2H, m, CH$_2$S); 3,10 (2H, m, CH$_2$N); 7,26 (2H, broad s, ArH).

Calcd for C$_{16}$H$_{23}$N$_3$S*H$_2$O: C 62,5; H 8,2; N 13,7; S 10,4. Found: C 62,7; H 8,0; N 13,6; S 10,5.

Dihydrochloride of XIV, yield 90%, p.decomp. 242–245° C. (from mixture abs. ethanol with ethylacetate).

Calcd for C$_{16}$H$_{23}$N$_3$S*2HCl*0,25H$_2$O: C 52,4; H 7,0; Cl 19,3; N 11,4; S 8,7.

Example 15. 2-[2-(Morpholino)ethylthio]-5,6-dimethylbenzimidazole(XV) and its dihydrochloride were synthesized as described above. The reaction of 2,67 g (0,015 mmol) 2-mercapto-5,6-dimethylbenzimidazole with 2,8 g (0,015 mol) 2-(morpholino)ethylchloride hydrochloride in the presence of 1,2 g (0,030 mol) sodium hydroxide gave in 69% yield of 2,95 g of compound XV, m.p. 147–148° C. (from ethylacetate with hexane). $^1$H NMR (CDCl$_3$), δ: 2,32 (6H, s, 2CH$_3$); 3,62 (4H, m, CH$_2$NCH$_2$ of morpholine); 2,86 (2H, m CH$_2$S); 3,21 (2H, m CH$_2$N); 3,83 (4H,m, CH$_2$OCH$_2$ of morpholine); 7,27 (2H, broad s, ArH).

Calcd for $C_{15}H_{21}N_3OS$: C 58,2; H 7,5; N 14,5; S 11,0. Found: C 58,0; H 7,3; N 14,5; S 11,1.

Dihydrochloride of XV, yield 96%, m.p. 250–252° C. (with decomp., from abs. ethanol).

Calcd for $C_{15}H_{21}N_3OS*2HCl$: C 49,4; H 6,4; Cl 19,5; N 11,5; S 8,8. Found: C 49,4; H 6,5; Cl 19,8; N 11,6; S 8,5.

Example 16. 2-[3-(Dimethylamino)propylthio]-5,6-dimethylbenzimidazole (XVI) and its dihydrochloride were synthesized as described above. The compound XVI was obtained from 2,67 g (0,015 mol) 2-mercapto-5,6-dimethylbenzimidazole and 2,78 g (0,019 mol) 3-(dimethyl) propylchloride hydrochloride in the presence 1,32 g (0,033 mol) sodium hydroxide in 73% yield (3,1 g), m.p. 95–98° C. (from ethanol with water). $^1H$ NMR ($CDCl_3$), δ: 1,91 (2H, m, $CH_2\underline{CH_2}CH_2$); 2,32 (6H, s, $2CH_3$); 2,34 (6H, s, $(CH_3)_2N$); 2,53 (2H, t, $CH_2S$); 3,18 (2H, t, $CH_2N$); 7,17 (2H, broad s, ArH).

Calcd for $C_{14}H_{21}N_3S*H_2O$: C 59,8; H 8,2; N 14,9. Found: C 59,8; H 8,2; N 14,7.

Dihydrochloride of XVI, yield 84%, m.p. 206–208° C. (with decomp., from mixture abs. ethanol with hexane).

Calcd for $C_{14}H_{21}N_3S*HCl$: C 50,0; H 6,9; Cl 21,1; N 12,5; S 9,5.

Example 17. 2-[3-(4-Methylpyperazino)propylthio]-5,6-dimethylbenzimidazole (XVII) and its trihydrochloride were synthesized as described above. The reaction of 2,8 g (0,010 mol) 2-mercapto-5,6-dimethylbenzimidazole and 3,74 g (0,015 mol) 3-(4-methylpyperazino)propylchloride dihydrochloride in the presence 1,32 g (0,033 mol) sodium hydroxide gave in 79% yield (2,5 g) compound XVII, m.p. 116–118° C. (with decomp., from chloroform with hexane). $^1H$ NMR ($CDCl_3$), δ: 1,95 (2H, m, $CH_2\underline{CH_2}CH_2$); 2,31 (6H, s, $2CH_3$); 2,35 (3H, s, $CH_3N$); 2,54 (10H, broad m, 8H of pyperazine, 2H, t, $CH_2S$); 3,22 (2H, t, $CH_2N$); 7,50 (2H, broad s, ArH). Trihydrochloride of XVII, yield 78%, m.p. 228–231° C. (with decomp., from ethanol).

Calcd for $C_{17}H_{26}N_4S*3HCl*H_2O$: C 45,9; H 7,0; Cl 23,9; N 12,6; S 7,2. Found: C 45,8; H 6,9; Cl 23,8; N 12,9; S 7,4.

Example 18. 1-Benzyl-2-[2-(dimethylamino)ethylthuo]benzimidazole (XVIII) and its dihydrochloride. To the suspension of 4,8 g (0,020 mol) 1-benzyl-2-mercaptobenzimidazole in the 10 ml water and 40 ml ethanol was added 1,8 g (0,044 mol) sodium hydroxide and was heated at 70° before dissolving of the precipitate. To the solution at 70° was added 3,16 g (0,022 mol) 2-(dimethylamino)ethylchloride hydrochloride. The reaction mixture was stirred for 3 hr, cooled, NaCl was filtered off and washed with ethanol. The solvent removed and was obtained the compound XVIII as an oil, which was dissolved in abs. ethanol, the solution was treated of ethanol with gaseous HCl. The precipitate was filtered , washed with abs. ether. The yield of dihydrochloride of XVIII was 5 g (62%), m.p. 190–191° C. (from ethanol). $^1H$ NMR ($D_2O$), δ: 3,15 (6H, s, $(CH_3)_2N$); 3,66 (2H, m, $CH_2S$); 3,94 (2H, m, $CH_2N$); 5,78 (2H, s, $CH_2Ar$); 7,43–8,0 (9H, m, ArH).

Calcd for $C_{18}H_{21}N_3S*2HCl*0,5H_2O$: C 54,9; H 6,1; Cl 18,0; N 10,7; S 8,9. Found: C 55,0; H 5,9; Cl 17,8; N 10,8; S 8,8.

Example 19. 1-Benzyl-2-[2-(diethylarnino)ethylthio]benzimidazole (XIX) and its dihydrochloride were synthesized as described above. The reaction of 4,8 g (0,020 mol) 1-benzyl-2-mercaptobenzimidazole and 3,8 g (0,022 mol) 2-(diethylamino)ethylchloride hydrochloride in the presence 1,8 g (0,044 mol) sodium hydroxide gave the compound XIX as an oil, which was converted into its dihydrochloride in 83%o yield, m.p. 136–137° C. (from abs. ethanol with ether). $^1H$ NMR ($D_2O$), δ: 1,37 (6H, t, $(\underline{CH_3}CH_2)_2N$); 3,34 (4H, q, $(CH_3\underline{CH_2})_2N$); 3,47 (2H, m, $CH_2S$); 3,79 (2H, m $CH_2N$); 5,75 (2H, s, $CH_2Ar$); 7,3–7,99 (9H), m, ArH).

Calcd for $C_{20}H_{25}N_3S*2HCl*0,5H_2O$: C 57,0; H 6,7; Cl 16,8; N 10,0; S 7,6. Found:. C 56,5; H 6,7; Cl 16,8; N 10,0; S 7,9.

Example 20. 1-(β-Phenylethyl)-2-[2-(dimethylamino)ethylthio]-benzimidazole (XX) and its dihydrochloride were synthesized as described above. The reaction of 2,54 g (0,010 mol) 1-(β-phenylethyl)-2-mercaptobenzimidazole and 1,73 g (0,012 mol) 2-(dimethylamino)ethylchloride hydrochloride in the presence of 1 g (0,025 mol) sodium hydroxide gave compound XX, which was turned into its dihydrochloride in 47% yield (1,7 g), m.p. 160–161° C. (from abs. ethanol with ether). $^1H$ NMR ($D_2O$), δ: 2,99 (6H, s, $(CH_3)_2N$); 3,27 (2H, t, $CH_2Ar$); 3,38 (2H, t, $CH_2S$); 3,55 (2H, t, $CH_2N$); 4,77 (2H, t, $CH_2N_{cycl.}$); 6,65–7,60 (9H, m, ArH).

Calcd for $C_{19}H_{23}N_3S*2HCl*0,5H_2O$: C 56,0; H 6,4; Cl 17,4; N 10,3; S 7,9. Found: C 56,3; H 6,0; Cl 17,6; N 10,3; S 7,9.

The solution of dihydrochloride in water was made neutral with solution of sodium bicarbonate, was extracted with ether, dried over anhydrous magnesium sulfate, filtered, the solvent was removed, the compound XX was obtained, m.p. 38–39° C. (petroleum ether). $^1H$ NMR ($CDCl_3$), δ: 2,33 (6H, s, $(CH_3)_2N$); 2,72 (2H, t, $CH_2S$); 3,06 (2H, m, $CH_2Ar$); 3,53 (2H, t, $CH_2N$); 4,31 (2H, s, $CH_2N_{cycl.}$); 7,10–7,70 (9H, m, ArH).

Calcd for $C_{19}H_{23}N_3S$: C 70,1; H 7,1; N 12,9; S 9,9. Found: C 70,1; H 7,1; N 12,9; S 9,8.

Example 21. 1-(β-Phenylethyl)-2-[2-(diethylamino)ethylthio]benzimidazole (XXI) and its dihydrochloride were synthesized as described above. The reaction of 2,54 g (0,010 mol) 1-(β-phenylethyl)-2-mercaptobenzimidazole and 2,1 g (0,012 mol) 2-(diethylamino)ethylchloride hydrochloride in the presence 1 g (0,025 mol) sodium hydroxide gave in 62% (2,2 g) compound XXI, m.p. 54–55° C. (from petroleum ether). $^1H$ NMR ($CDCl_3$), δ: 1,05 (6H, t, ( $\underline{CH_3}CH_2)_2N$); 2,61 (4H, q, $(CH_3\underline{CH_2})_2N$); 2,84 (2H, t, $CH_2S$); 3,04 (2H, m, $CH_2Ar$); 3,47 (2H, t, $CH_2N$); 4,28 (2H, m, $CH_2N_{cycl.}$); 7,09–7,70 (9H, m, ArH).

Calcd for $C_{21}H_{27}N_3S$: C 71,3; H 7,7; N 11;9. Found: C 71,4; H 7,7; N 11;7.

Dihydrochloride of XXI was obtained in 67% yield, m.p. 129–130° C. (from abs. ethanol with ethylacetate). $^1H$ NMR ($CDCl_3$), δ: 1,38 (6H, t, $(\underline{CH_3}CH_2)_2N$); 3,26 (2H, t, $CH_2Ar$); 3,24 (2H, m, $CH_2S$); 3,35 (4H, q, $(CH_3\underline{CH_2})_2N$); 3,54 (2H, m, $CH_2N$); 4,76 (2H, t, $CH_2N_{cycl.}$); 6,9–7,9 (9H, m, ArH).

Calcd for $C_{21}H_{27}N_3S*2HCl$: C 59,1; H 6,9; Cl 16,6; N 9,9; S 7,5. Found: C 59,1; H 6,8; Cl 16,3; N 10,0; S 7,3.

Example 22. 1-(β-Phenylethyl)-2-[2-morpholino)ethylthio]benzimidazole (XXII) and its dihydrochloride were synthesized as described above. The reaction of 2,54 g (0,010 mol) 1-(β-phenylethyl)-2-mercaptobenzimidazole and 2,04 g (0,011 mol) 2-(morpholino)ethylchloride hydrochloride in the presence of 1 g (0,025 mol) sodium hydroxide gave in 73% yield (2,7 g) compound XXII, m.p. 66–67° C. (from hexane). $^1H$ NMR ($CDCl_3$), δ: 2,51 (4H,m, $CH_2NCH_2$ of morpholine); 2,74 (2H, t, $CH_2S$); 3,04 (2H, m, $CH_2Ar$); 3,51 (2H, t, $CH_2N$); 3,70 (4H, m, $CH_2OCH_2$ of morpholine); 4,31 (2H, m, $CH_2N_{cycl.}$); 7,05–7,70 (9H, m, ArH).

Calcd for $C_{21}H_{25}N_3OS$: C 68,6; H 6,9; N 11,4; S 8,7. Found: C 68,5; H 7,0; N 11,5; S 8,9.

Dihydrochloride of XXII was obtained in 70% yield, m.p. 179–180° C. (from abs. ethanol with ethylacetate). $^1H$ NMR ($D_2O$), δ: 3,28 (2H, broad t, $CH_2Ar$); 3,37 (2H, m, $CH_2S$); 3,44 (4H, $CH_2NCH_2$ of morpholine); 3,58 (2H, m, $CH_2N$); 4,08 (4H, m, $CH_2OCH_2$ of morpholine); 4,76 (2H, broad t, $CH_2N_{cycl.}$); 6,9–7,9 (9H, m ArH).

Calcd for $C_{21}H_{25}N_3OS*2HCl$: C 57,3; H 6,2; Cl 16,1; N 9,5; S 7,3. Found: C 57,1; H 5,8; Cl 15,8; N 9,8; S 7,8.

The Industrial Usage

The Results of the Pharmacological Study of Applied Compounds

For revealing an anxiolytic effect of the new compounds the measurement of locomotor activity in the "open-field" test which allows to estimate not only the expression of anxiolytic effect but also the degree of its selectivity [Seredenin S. B. et al., Bull.Exp.Biol.Med., 1979, v.88, N7, p.38; Seredenin S. B. et al., in: "Drug Dependence and Emotional Behavior", Ed. by Valdman A. V., Consult Bureau, New-York, London, 1987, p.49–77] was used. The main point of this approach consists in comparative analysis of the behavioural effects of tested compounds in two inbred strains of mice Balb/c and C57Bl/6 with different hereditary types of emotional-stress reactions (ESR). The anxiolytic effect was estimated as the activation of the locomotor activity of animals with "passive" type of ESR (Balb/c mice). The main index describing the sedative properties of tested drugs was the inhibition of the locomotor activity of mice with "active" type of ESR (C57Bl/6 strain). The anxioselectivity was evaluated according to coincidence of doses range which activated or inhibited the behavior of mice of different strains. Earlier this approach has been successfully used for estimation of anxioselective activity of such known drugs as phenazepam [Seredenin S. B. et al., Bull.Exp.Biol.Med., 1979, v.88, N7, p.38; Seredenin S. B. et al., Ann.Inst.Super.Sanita, 1990, v.26, N1, p.81–88], mexidol [Seredenin S. B. et al., Khimiko-Farmatsevt.Zhurnal, 1987, N2, p.134; Vironina T. A., Seredenin S. B., Ann.Inst.Super.Sanita, 1988, v.24, N3, p.461–466] and gidazepam [Seredenin S. B. et al., in: "Gidazepam" Kiev, Naukova Dumka, 1992, p.92; Seredenin S. B., Blednov Yu. A., Phys.Chem.Biol.Med., 1993, v.1, N1, p.53–60].

Male C57Bl/6 and Balb/c mice ("Stolbovaya" animal farm), weighing 20–22 g were used. The animals were housed in a separate animal room in groups of ten and maintained on 12 h light-dark cycle (light from 8.00 till 20.00) with free access to standard food and water during two weeks before experiment. Testing was performed between 9.00 and 13.00. Every used compound was administered intraperitoneally in water solutions 30 min before testing (0,1 ml solution per 10 g of weight). The "open-field" apparatus consisted of cylinder closed from one end, illuminated by four 75 W lamps fixed to the walls 100 cm above the floor. The "open-field" apparatus was 100 cm in diameter and white-painted; the floor was marked with 3 black circles and some radial lines divided the floor into 16 peripheral and 8 central segments. 30 min after injection each animal was placed in the same peripheral square on the floor for 3 min of testing after 1 min exposure in the dark chamber. The following behavior variables were recorded: 1) the number of crossings in the peripheral area (peripheral activity); 2) the number of crossings in the central segments (central activity); 3) the number of rearings (vertical activity); 4) the emotionality was measured as the number of defecations during the test. The sum of all types of locomotor activity was marked as total activity. The t-Student test was used for statistical analysis.

The results obtained in screening experiments with usage of genetic models allow to divide the tested compounds into 3 groups:

1. The compounds I, VIII, X, XI, XXI and XXII had neither activatory nor inhibitory effects on the behavior of mice with "passive" type of emotional-stress reaction (Balb/c strain) in "open-field" test.
2. On the contrary, the compounds VI (Tab.1), XVI (Tab.2), XVII (Tab.3) and XIX (Tab.4) inhibited the locomotor activity of Balb/c mice in "open-field" test with different degree. These results confirm the absence of tranquillising-activatory effect of these drugs, but do not exclude the presence of expressed tranquillising-sedative activity (proceeding from low active doses).
3. At last, there were found some compounds: III (Tab.5, 6), IV (Tab.7,8), IX (Tab.9,10), XII (Tab.11,12), XIII (Tab.13,14),. XIV (Tab.15,16) and XV (Tab.17,18) which were able to activate the behavior of Balb/c mice in "open-field" test in wide doses range without any changes in locomotor activity of animals with "active" type of emotional-stress reaction (C57Bl/6 strain). These data indicate the presence of expressed selective tranquillising-activatory effect.

The 4 compounds from earlier revealed 3rd group (IV, XII, XIV and XV) demonstrated more expressed anxioselective action at the first stage of experiments have been choosen for further more profound study of tranquillising effect and estimation of possible side effects.

The study of anxiolytic activity of chosen compounds was carried out in the experiments with outbred male rats weighing 180–200 g in standard conflict Vogel' procedure [Voronina T. A. et al., in: "Phenazepam", Naukova Dumka, Kiev, 1982, p.89, 93, 146]. The main aim of the initial step of experiments was the training of rats to develop the feeling of thirst with following experience of water licking from bottle in the experimental chamber. The animals were deprived of water for 24 hours and were placed in the test chamber for 5-min adaptation period during which they had free access to the drinking bottle. After another 24 h deprivation period the rats were placed again in the test chamber and were allowed to drink water for 5 sec. Immediately afterwards drinking attempts were punished by electric shock (0,5 mA). Under this collision of drinking and protective reflexes the extremal situation was developed. In this situation the anxiety of punishment prevented the licking process. The number of shocks received throughout a 5-min experimental session was recorded.

In this test the control animals made from 8 to 14 attempts of punished lickings (Tab.19). The compounds IV, XII, XIV and XV at doses from 1 mg/kg to 20 mg/kg (i.p.) produced the anticonflict (anxiolytic) effect. It was expressed in 2–4 times enhancement of punished licking of water in comparison with control. Proceeding from results obtained in these experiments we can conclude, that the compounds IV, XII, XIV and XV possessed expressed anxiolytic properties in wide dose range.

The myorelaxant activity of choosen compounds were studied in the outbred male mice weighing 22–25 g in rotarod test [Voronina T. A. et al., in: "Phenazepam", Naukova Dumka, Kiev, 1982, p.145]. The animals were placed on the horizontal rotarod (D=2 cm) calibrated for a fixed speed of 4 rpm. According to the rotarod experimental protocol, normal motor coordination was defined by the ability of the animals to remain on the rotarod for an arbitrarily selected time of 120 sec. Data presented in Tab.20 show that the compound XII at dose range of 0,01 mg/kg–50 mg/kg has no effect on the motor coordination. The similar results were obtained for compounds IV, XIV and XV tested at doses of 0,1 mg/kg–20 mg/kg. Thus, the data obtained in this test demonstrate the absence of myorelaxant activity for any used compound.

The possible hypnotic effects of choosen drugs was estimated according to method of potentiation of sleep induced by sodium thiopental. The male outbred mice weighing 20–25 g were injected i.p. with sodium thiopental at dose of 70 mg/kg. Two parameters were estimated: latent time of sleeping and duration of sleep. The used compounds were administered i.p. 30 min prior injection of sodium thiopental. Data presented in Tab.21 demonstrate that every tested drug has no effects on both the latent time of sleeping and duration of sleep (Tab.22).

The acute toxicity was measured in outbred mice after per os administration of used drugs in the 1% starch suspension. The lethal doses were calculated according to Litchfield-Wilcocson' method. The $LD_{50}$ value for compound XII was 1,16 g/kg (95% probability: 0,89–1,48 g/kg) and was very close to $LD_{50}$ for another derivative of 2-mercaptobenzimidazole known as bimityl. Thus, we can conclude that the compound XII is not toxic.

The Effects of Choosen Compounds on the Cardiovascular System

The pharmacological studies of salts of applied compounds were carried out in different models of ischemia and cardiac arrhythmia in comparison with the standard drugs such as dihydroxychloride 2-[2-(diethylamino)ethylthio]-5, 6-dimethylbenzimidazole (XXIII), verapamil, propranolol, novocainamide, quinidine, lidocaine, bonnecor.

Anti-ischemic Activity

The effects of compounds on the hemodynamics and activity of intact heart were studied in cats under anesthesia. The experiments were carried out under conditions of open chest. The phase curve of aortic blood flow was the main index of cardiac activity. The compounds were administered i.v. in physiological solution. The t-Student' test was used to estimate the statistical significance.

It was shown that the compound VIII (1,0 mg/kg), IX (0,5 mg/kg and 1,0 mg/kg) and XX (1,0 mg/kg and 2,0 mg/kg) induced the expressed bradycardia which lasted for 30 min after administration. The value of double product which is the indirect index of heart oxygen consumption also diminished. It is necessary to take into account that the decrease in heart oxygen consumption is one of the main indexes of antianginal drugs [Kaverina N. V., Rozonov Y. B., Chichkanov G. G.: The modem aspects of the pharmacology of antianginal drugs, M., Meditsina, 1980, p.240]. The bradycardia induced by used compounds was accompanied by the enhancement of stroke volume. Another parameters of hemodynamics were not in fact changed (Tab.23,24,25). The prototype-compound XXIII [Saveliev V. L., Moshaeva T. Ya., Chichkanov G. G et al.: The application N 4951704/04 (1991) for patent of Russia, positive decision on 26.10.1993] also induced the expressed and long bradycardia. However, during 2–3 min after its administration the system blood pressure and mean aortic blood flow acceleration also diminished. This fact indicates the inhibition of contractile function of heart (Tab.26). The second comparative drug-verapamil also induced the bradycardia and inhibited the contractile function of the heart (Tab.27). On the contrary, the compounds VIII, IX and XX did not inhibited but even slightly enhanced the contractility of myocardium (the tendency toward the enhancement of this parameter appeared).

The compounds VI, X, XII, XVII and XXI at doses of 0,5 mg/kg–2,0 mg/kg produce a small and short bradycardia and have no effects on the other parameters of hemodynamics and heart activity.

The compound XV induces the small, but statistically significant bradycardia at a dose of 5 mg/kg.

The compounds XI, XVI, XVIII, XIX and XXII have no effects on the parameters of hemodynamics and heart activity. Basing on these results the compounds VIII, IX and XX have been choosen for further indepth investigation.

To demonstrate of protective effect of used drugs on the ischemized myocardium it was necessary to carry out the experiments in the model of acute coronary deficiency. These experiments were conducted in cats weighing 2,5–4,0 kg under anasthesia by i.v. injection of nembutal (40 mg/kg) in open chest conditions. Epicardium electrogram in 3–4 leads was registered in "Mingograph-81". The value of mean elevation of ST-segment during 5 min occlusions of anterior left descending coronary artery with 15 min reperfusions between them was the main index of intensity of reversible ischemized damage of myocardium. The adequacy of this model was earlier verified with propranolol, nitroglycerin and verapamil which produced the expressed anti-ischemic action [Tsorin I. B.: Ph.D Dissertation, M., 1985, p.148].

The statistical calculation was carried out with non-parametric Wilcocson method for associated variants.

There were carried out two series of experiments 6–7 animals in each. The results obtained from these experiments have shown that the compounds VIII and IX at a dose of 1,0 mg/kg (i.v.) decreased the mean elevation of ST-segment in multiple leads of epicardium electrogram during 5 min occlusion of coronary artery. But if the compound VIII was effective immediately after occlusion, the compound IX produced the anti-ischemic effect during 40 min after its injection (Tab.28,29). The prototype XXIII has a similar effect in this model, but only under its permanent infusion. After bolus injection its effect was very short (FIG. 1). Verapamil also improves the functional state of ischemic focus in this model but with expressed inhibition of contractility heart function [Tsorin I. B.: PhD Thesis, M., 1985, p.148].

Thus, the compounds VIII and IX produced the anti-ischemic action, which is probably associated with the decrease in heart oxygen consumption as the result of induced bradycardia. The advantage of tested novel compounds in comparison with prototypes (compound XXIII and verapamil) is the induction of bradycardia without inhibition (even for a short time) of myocardium contractility function.

The presented data allowed to suggest that the compounds VIII and IX belong to the novel group of antianginal drugs—selective bradycardic agents like Falipamil (structural analogue of verapamil). The wider study of activity of the compound IX has been carried out to confirm this assumption.

The effects of this compound on contractile and pump functions of ischemized myocardium were studied in cats weighing 3,0–4,5 kg under anesthesia with nembutal (40 mg/kg). Under open chest conditions the occlusion of anterior left descending coronary artery was carried out for 20–40 min and it was changed by 30–50 min reperfusion respectively. The phase curve of blood flow in ascending part of the aortic arch was recorded with electromagnetic blood flowmeter MFV-1200 ("Nihon-Kohden", Japan). Hemodynamics, heart activity values and the number of arrhythmia were calculated. In the experiments with 40 min ischemia immediately after 60 min the intact and ischemized zones of left ventricle were dissected and freezed in liquid nitrogen. ATP level was measured using hexokinase method in these zones. 4 series of experiments (2-control and 2-basic) were conducted in 12 cats in each. For statistical calculation the t-Student and Fisher's precision test were used.

Figure 2:
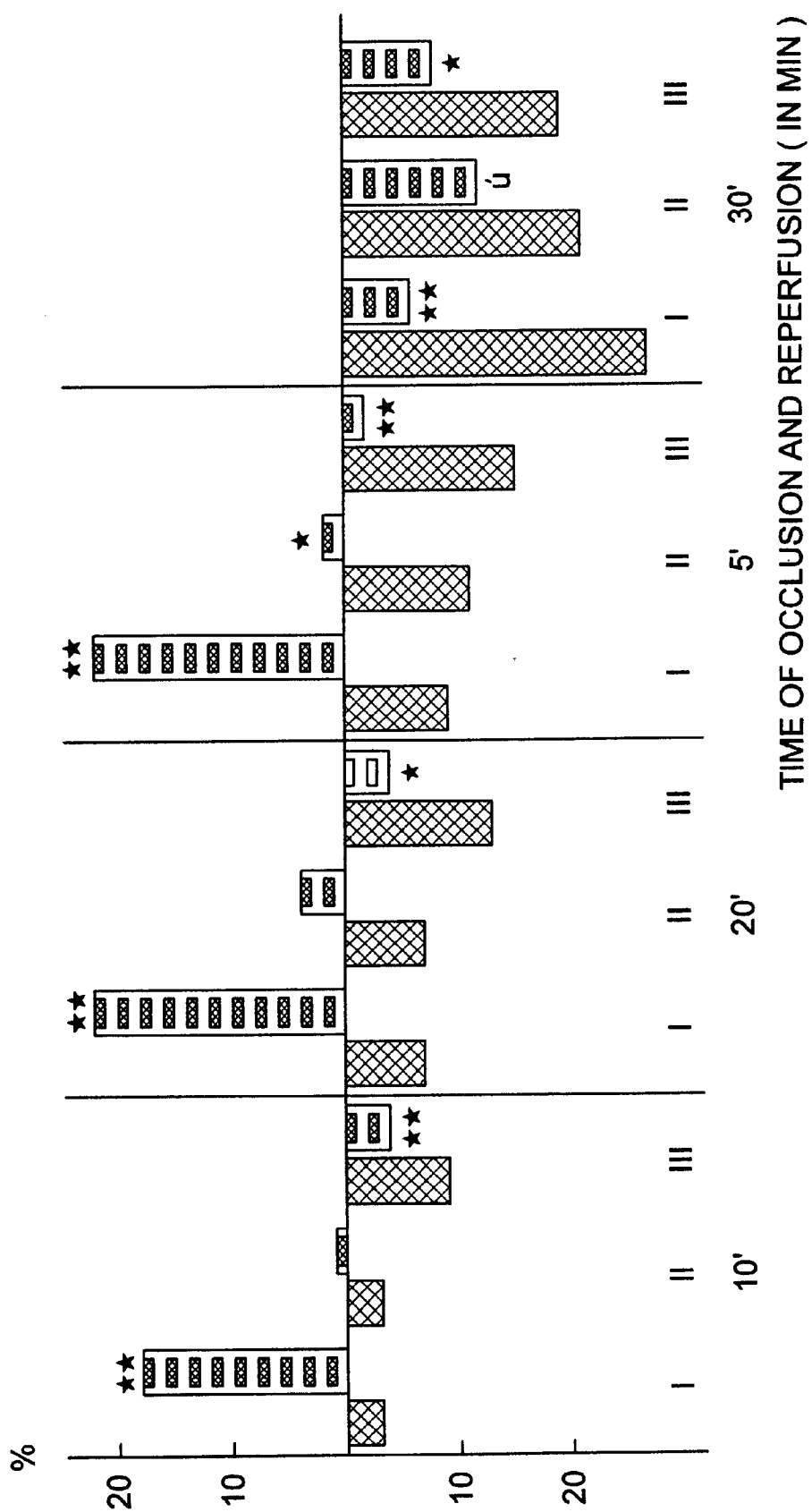

The data obtained from these experiments have shown that compound IX (bolus injection at a dose of 1,0 mg/kg immediately after occlusion +50 mcg/kg/min i.v. during 30 min) under conditions of 20 min occlusion with following 30 min reperfusion significantly prevents the inhibition of contractile function of myocardium induced by ischemic damage. The action of compound IX lasted throughout the experiments while the effect of prototype XXIII was observable only during occlusion period and first 10 min of reperfusion. The compound IX prevented the decrease in cardiac output. But the the cardiac output remained steady to less extent that is probably due to expressed bradycardia induced by these drugs (FIG. 2,3).

It is necessary to stress that in control experiments different types of arrhythmia appeared very often during occlusion and reperfusion periods. The compound IX decreased the number of arrhythmias which occurred under these conditions.

Figure 4A:
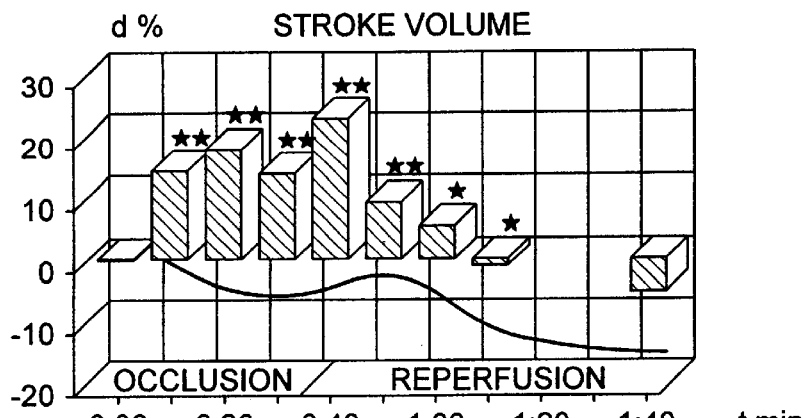
Figure 4B:
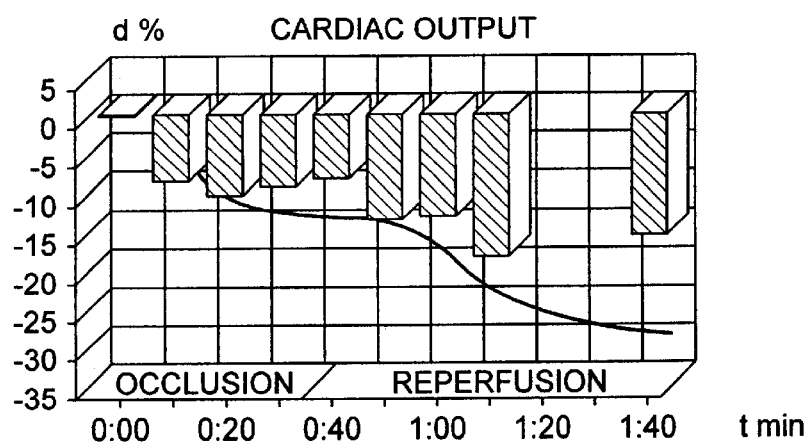
Figure 4C:
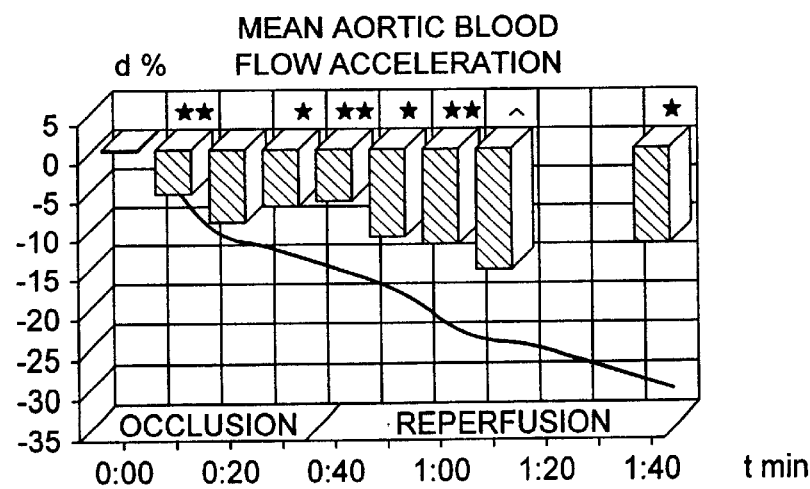

Under critical ischemia (40 min occlusion and 60 min reperfusion of coronary artery) the compound IX prevented the inhibition of contractile function of heart induced by ischemic damage of myocardium. This compound also prevented the decrease in stroke volume and had no effect on changes in cardiac output (FIG. 4). Under conditions of critical and mild ischemia the compound IX did not reduced the number of arrhythmias induced by occlusion and reperfusion of coronary vessel.

Figure 5:
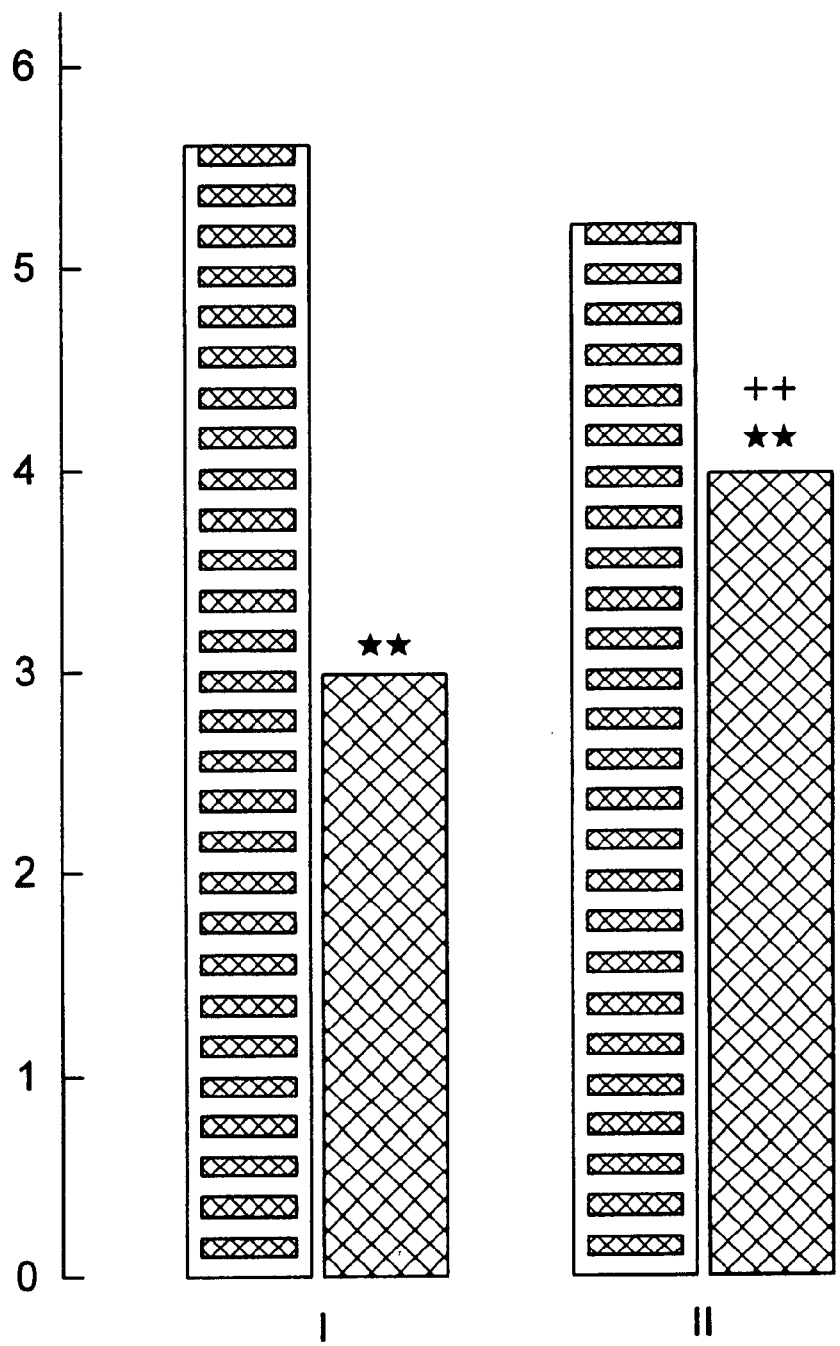

After 40 min occlusion and 60 min reperfusion of coronary artery in ischemized myocardium the ATP level significantly declined (−46,4±5,6%) when compared with intact area. The compound IX increased the ATP level in the ischemized myocardium and did not change it in the intact zones. At the same time the prototype did not change the ATP level (FIG. 5).

Thus, the compound IX under ischemia of different duration with following reperfusion prevents the inhibition of pump and contractile functions of heart. This compound increases the ATP level in the ischemized myocardium in comparison with prototype.

It is well known that the classic bradycardic compounds like alinidine and falipamil demonstrate an expressed antiarrhythmic effect. In this respect it was interesting to study the effect of compounds IX and XX in different models with disturbances of cardiac rhythm.

Antiarrhythmic Activity

Antiarrhythmic properties of applied compounds were studied in adrenaline model in concious rabbits, in calcium chloride and aconitine models in concious rats, in the model of ventricular fibrillation in anesthetized rats and in Harris's model in concious dogs.

Adrenaline arrhythmia. The 0,1% solution of adrenaline hydrochloride was injected to the marginal ear's vein of rabbit weighing 2,5–3,0 kg at dose ranging 120–150 mcg/kg which induced cardiac rhythm disturbances of two types. In one case immediately after injection of very high doses of adrenaline (150–160 mcg/kg) the polyfocus extrasystoles occurred and was changed by ventricular tachycardia and fibrillation. In other cases the ventricular extrasystole occurred on the background of bradycardia with atrioventricular block of different extent which was transformed to polyfocus extrasystoles and ventricular tachycardia in 2–3 min. In this case the bradycardia had a reflex character and developed as response to the enhancement of blood pressure induced by adrenaline.

The tested compound was injected in 3 ml of distilled water 30 min after determination of arrhythmogenic dose of adrenaline and the ECG was recorded in 2nd standard lead. 2 min after administration of tested compound the arrhythmogenic dose of adrenaline was injected. The antiarrhythmic efficacy of tested compound was determined according to its ability to prevent the rabbit's death as the result of lethal ventricular fibrillation and appearance of arrhythmia. Data presented in Tab.30 show that the compounds IX and XX induce the similar antiarrhythmic effect as verapamil and propranolol (antiarrhythmic agents of the 4th and 2nd classes respectively). But the antiarrhythmic effect of tested compounds was higher when compared with quinidine and lidocaine (antiarrhythmic drugs of the 1st class).

Calcium Chloride Arrhythmia in Rats.

In these experiments the outbred concious rats 180–200 g of weight were injected with 10% solution of calcium chloride in tail vein at dose range of 250–300 mg/kg. Usually the ventricular fibrillation occurs 1–2 min after injection. But sometimes immediately after injection the expressed synus bradycardia with ventricular extrasystole transforming to volley of ventricular tachycardia with final ventricular fibrillation develop. The injection of tested compounds IX and XX 2 min prior calcium chloride administration prevents the death of animals as the result of lethal venricular fibrillation. The mean effective doses of the compounds IX and XX were 1,0 mg/kg and 2,03 mg/kg respectively and this is indicative of their high antiarrhythmic activity. As to the activity of the compound IX it was 50-folds and 7,5-folds higher than that of the novocainamide and lidocaine respectively.

Aconitine arrhythmia. The aconitine arrhythmia was induced in concious rats weighing 180–200 g by the injection in tail vein of the aconitine sulfate solution at dose range of 40–50 mg/kg. Mixed atrioventricular disturbances of rhythm (usually the polyfocus extrasystole) were observed. The tested compounds were administered i.v. 3 min prior aconitine injection. The $ED_{50}$ value was calculated according to Litchfield's method.

The results obtained from the study in this model have shown that the compound IX produced a high activity: $ED_{50}$=1,2 mg/kg, $LD_{50}$=31,5 mg/kg (after i.v. injection), the antiaarhythmic index ($LD_{50}/ED_{50}$)=26,2 (Tab.30). The activity of this compound was higher than that of the known antiarrhythmic drugs of the 1st class as quinidine and lidocaine in 4,4-folds and 6,5-folds respectively. The spectrum of its therapeutic action was also wider if compared with the standard drugs.

The Study of Antifibrillartory Properties of Compounds IX and XX in Rats

The experiments were conducted in male rats weighing 180–240 g and anesthetized with nembutal (60 mg/kg i.v.) with open chest and artificial respiration. The occlusion of the left coronary artery was performed 1–2 min after experiment beginning with following reperfusion after 7 min. During this period time according to literature data [Krzeminski T., Grzyb J., Kurcok A., Brus R.: Pol.J.Pharmacol., 1992, 44, Suppl., p.169–170] the maximum number of ventricular fibrillations (70–100%) were registered. The ECG in the 2nd standard lead was recorded in "Mingograph-81". The number of ventricular fibrillations during occlusion and reperfusion periods, the life menacing arrhythmia (fibrillation+paroxysmal ventricular tachycardia) and total number of arrhythmias were calculated. The known antiarrhythmic drug bonnecor was used as the reference agent [Grigorieva E. K., Gorbunova V. V. in: "New antiarrhythmic drug—bonnecor (the pharmacology and clinical usage)", M., 1993, p.64–67]. The compounds were injected i.v. at the following doses: bonnecor—1,0 mg/kg, compound IX—2,0 mg/kg, compound XX—1,0 mg/kg. The control animals were administered with the equivalent volume of physiological solution (1,0 ml/kg). 4 series of experiments were carried out in 80 rats. The results were assessed according to the method of point scale: the absence of arrhythmia—0 point, extrasystole—1 point, paroxysmal ventricular tachycardia—2 points, ventricular fibrillation—3 points, fibrillation observed during the occlusion of coronary vessel—4 points. For statistical analysis the Fisher's exact probability and Wilconson's methods were used.

[Krzeminski T., Grzyb J., Kurcok A., Brus R.: Pol.J.Pharmacol., 1992, 44, Suppl., p.169–170] have shown that 7 min occlusion with following reperfusion of coronary artery in anesthetized rats produced the ventricular fibrillation (68–100%). Defibrotide and prostacycline decreased the number of fibrillations. We have studied the antifibrillator activity of some derivatives of 2-mercaptbenzimidazole in this model with disturbances of heart rhythm. Bonnecor (1,0 mg/kg) was used as the reference drug. It is well known that this agent produces apronouncedantifibrillatoryactivity [Grigorieva E. K., Gorbunova V. V. in: "New antiarrhythmic drug-bonnecor (the pharmacology and clinical usage)", M., 1993, p.64–67].

The data obtained from the control experiments have shown that ventricular fibrillations were observed in 15 cases out of 24 (62,5%) and lethality hazardous arrhythmia (fibrillation+paroxysmal ventricular tachycardia)—in 22 cases (91,7%). Under these conditions bonnecor decreased the number of both the ventricular fibrillations and lethality hazardous arrhythmia. Not only the total number but the degree of arrhythmias expression decreased (according to point scale calculations).

The compound IX at a dose of 2,0 mg/kg like bonnecor also reduced the number of both the ventricular fibrillations and lethality hazardous arrhythmia (Tab.31). The compound X at a dose of 1,0 mg/kg was characterised only by a trend to decrease the number of ventricular fibrillations, but it significantly reduced the number of arrhythmia hazardous for life and their manifestation degree (tab.31).

Thus, the tested compounds produced the antifibrillatory effect. We would like to note that classic drug with bradycardic type of action—alanidine also has the antifibrillatory effect [Uprichard A. C. G., Chi J. J. et al., J.Cardiovas.Pgarmacol., 1989, 14, p.475–482].

The arrhythmia in concious dogs according to Harris. The experiments were conducted in mongrel dogs of either sex weighing 9–14 kg. Under anesthesia (40 mg/kg of nembutal i.v.) and artificial respiration the two-step occlusion of the left anterior descending coronary artery was performed. The constant ECG disturbances of the heart rhythm were recorded after 24 hours. The compounds IX and XX were injected iv. in water solutions at a dose of 2,0 mg/kg. T-Student' test was used for statistical calculation.

The results obtained from these experiments have demonstrated that the compound IX produced the gradual bradycardia. The antiarrhythmic effect of this drug was revealed in every used animal and continued for 50 min in spite of a high basal level of the ectopic activity. The duration of the prototype XXIII effect shorter (Tab.32,33). On the background of compound IX effect the mild excitation was usually observed. Most probably this excitation is the main reason preventing the development of the pronounced bradycardia immediately after drug administration.

Figure 6:
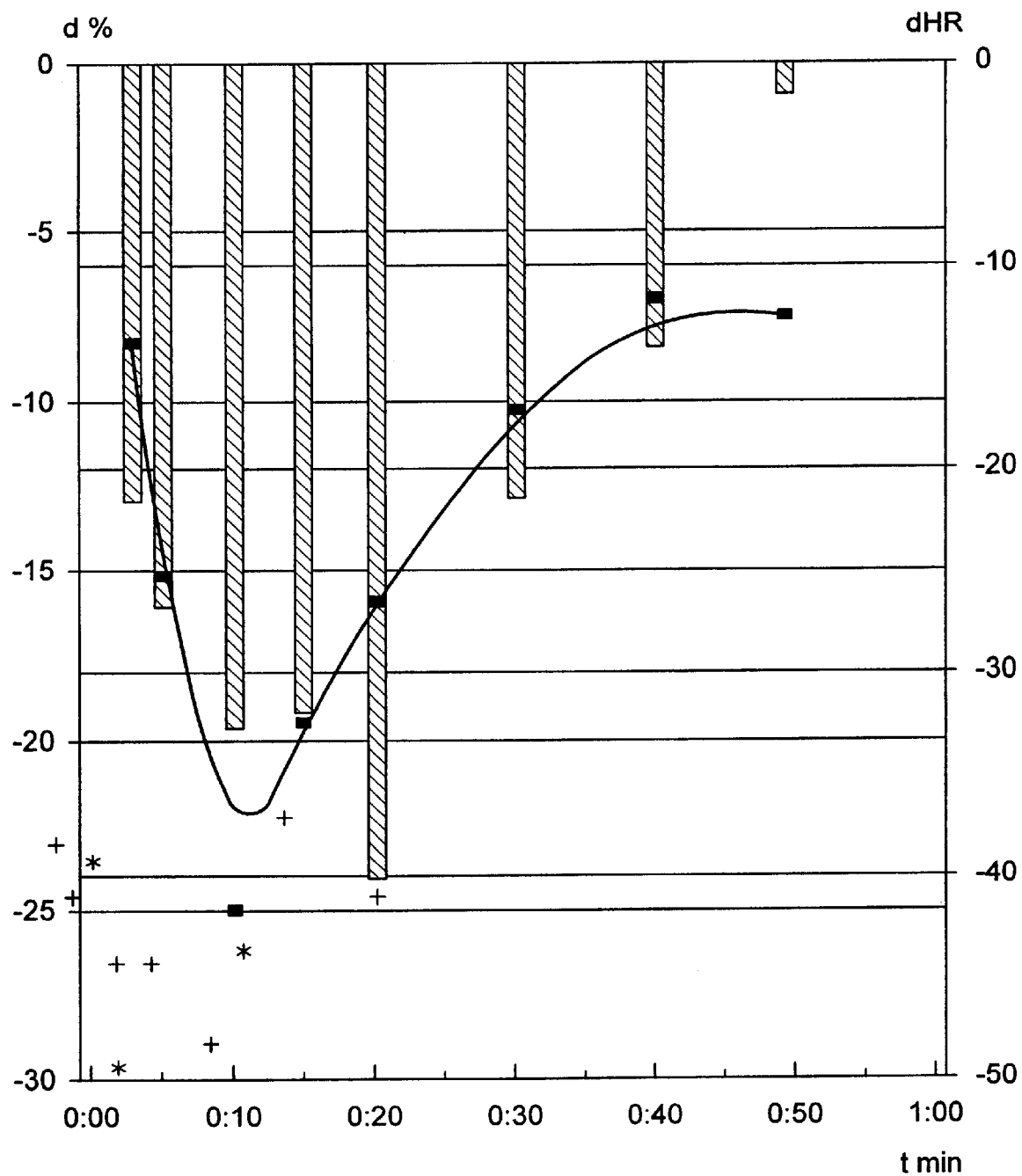

The compound XX also produced the pronounced bradycardia independently on basal level of ectopic activity. This drug also induced the antiarrhythmic effect (Tab.34; FIG. 6). In the experiments with high level of ectopia (N1 and N4) the antiarrhythmic effect was weak and present only for 10–15 min. In the experiment with mild ectopic activity (N3) the complete block of compound-induced arrhythmia was revealed. In this case the tendency to restore the arrhythmia was marked only in 30–40 min. In the experiment N2 the antiarrhythmic effect was weak and short. It is important that even in the experiments when the antiarrhythmic effect was weak (according to percent calculations of ectopic contractions) the compounds XX had the positive action. It prevented the paroxysms of ventricular tachycardia and extrasystoles and induced the development of steady rhythm. The compound XX is well tolerated by the animals and possessed some sedative activity.

Thus, the compounds IX and XX produce the the pronounced antiarrhythmic effect and have no side effects in concious dogs with ventricular disturbances of heart rhythm.

So, some compounds were revealed among 2-mercaptobenzimidazole derivatives which produce the expressed bradycardia and have no effects on the other parameters of hemodynamics and heart function. This fact allows to refer these compounds to the group of specific bradycardic agents. These compounds also possess the expressed anti-ischemic and antiarrhythmic actions.

DESCRIPTIONS OF FIGURES

FIG. 1. The effects of the compound XXIII (1,0 mg/kg+50 mcg/kg/min i.v.) on the mean value of the ST segment elavatation in the epicardiac electrogramm during 5-min occlusion of coronary artery. Ordinate axis—mean ST segment elevation in mV; absciss axis—time of the occlusion and the reperfusion of coronary artery in min. 1—control occlusion; 2—the occlusion immediately after beginning of compound injection; 3—in 20 min. *–$P<0,05$; ^–$P<0,1$ in comparison with control occlusion.

FIG. 2. The effects of the compound IX on the pump and contractile heart function under conditions of 20-min occlusion and 30-min reperfusion of the coronary artery. Ordinate axis—changes in comparison with basal level in %; absciss axis—time of the occlusion and reperfusion in min. I—stroke volume; II—cardiac volume; III—mean accelaration of blood flow in aorta. ■-control; ▬-compound IX. ú–$P<0,1$; *–$P<0,05$; **–$P<0,01$ in comparison with control.

Figure 3:
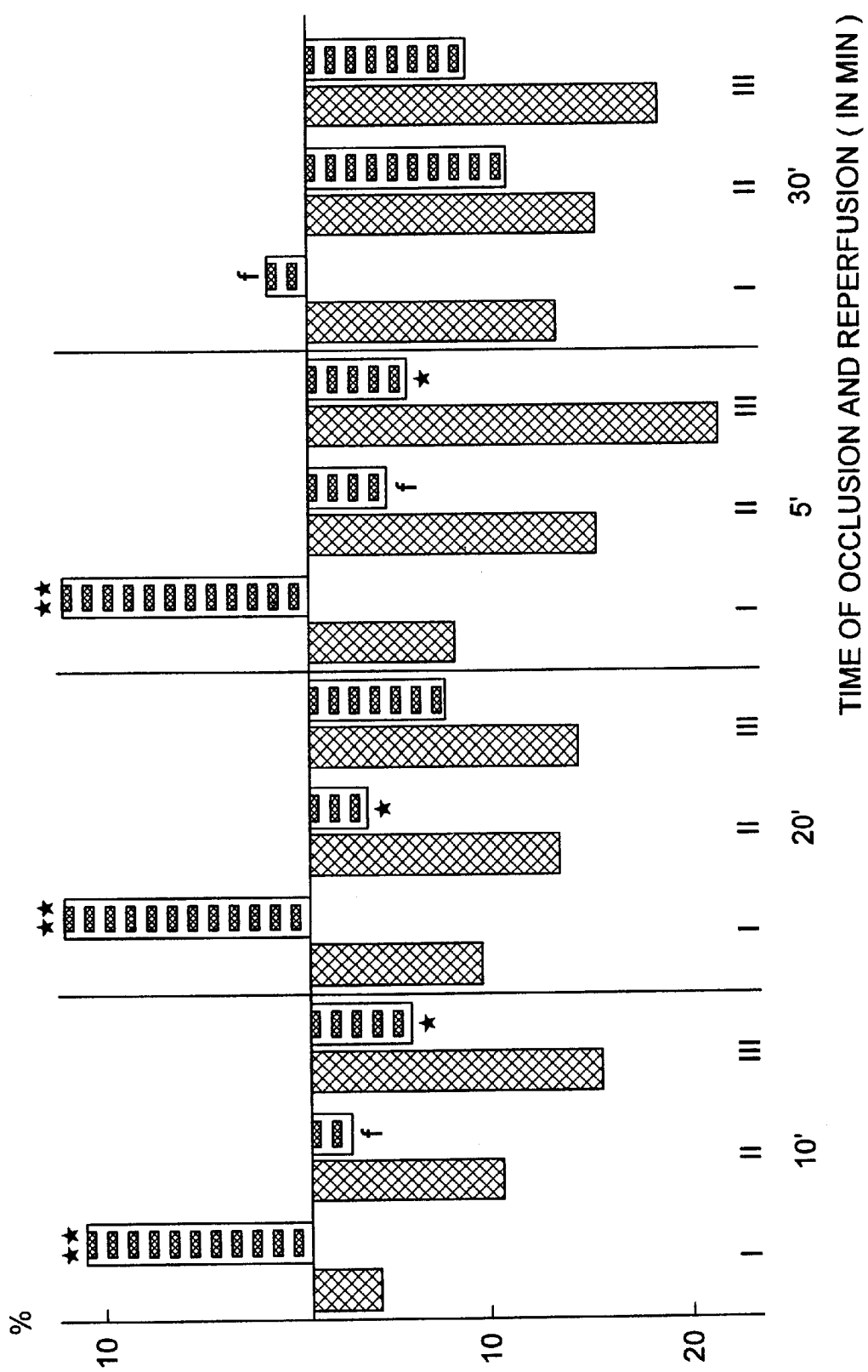

FIG. 3. The effects of the compound XXIII on the pump and contractile heart function under conditions of 20-min occlusion and 30-min reperfusion of the coronary artery. Ordinate axis—changes in comparison with basal level in %; absciss axis—time of the occlusion and reperfusion in min. I—stroke volume; II—cardiac volume; III—mean accelaration of blood flow in aorta. ■-control; ▬-compound IX. ú–$P<0,1$; *–$P<0,05$; **–$P<0,01$ in comparison with control.

FIG. 4. The effects of the compound IX on the hemodynamics and heart activity under conditions of 40-min occlusion and 60-min reperfusion of the coronary artery. Ordinate axis—changes in the parameters in %; absciss axis—time of the occlusion and reperfusion in min. The curve—control; columns—compound IX. ^–P<0,1; *–P<0,05; **–P<0,01 in comparison with control.

FIG. 5. The effects of the compound IX on the ATP level in intact and ischemized myocardium of the left ventricule of cat after 40-min ocllusion and following 60-min reperfusion of the coronary artery. ▪-intact zone of myocardium from the ischemized left ventricule; ▪-ischemized zone of myocardium. I—control; II—compound IX. Ordinate axis—the level of ATP in mcM/g of wheight. **–P<0,02 in comparison with intact zone; ++–P<0,02 in comparison with control.

FIG. 6. The effects of the compound XX (1,0 mg/kg i.v.) on the ectopic activity of heart in concious dogs according to Harris. Left ordinate axis—the changes in the of frequency of the ectopic contractions in % (curve); Right ordinate axis—the changes in the heart rate in beats/min (columns); absciss axis—time after injection of the compound in min. *–P<0,05 in comparison with basal level of ectopic activity; +–P<0,05 in comparison with basal level of the heart rate.

TABLE 1

The effect of compound VI on the behavior of Balb/cmice in "open-field" test (M ± $m_x$).

| Doses (mg/kg) | Types of activity | | | | |
|---|---|---|---|---|---|
| | Peripheral | Central | Vertical | Number of defecations | Total |
| Control n = 8 | 8.8 ± 1.6 | — | — | 1.0 ± 0.7 | 8.8 ± 1.6 |
| 0.1 n = 8 | 3.0 ± 1.8 * | — | — | — | 3.0 ± 1.8 * |
| 1.0 n = 9 | 3.3 ± 1.3 * | — | 0.4 ± 0.4 | — | 3.7 ± 1.7 * |
| 10.0 n = 8 | 3.1 ± 0.8  | — | — | — | 3.1 ± 0.8  | n - number of animals; *,  N * - statistically significant from correspondent control (P<0.05, P<0.01 and P<0.001 respectively, t-Student test).

TABLE 2

The effect of the compound XVI on the behavior of Balb/c mice in "open-field" test (M ± $m_x$)

| Doses (mg/kg) | Types of activity | | | | |
|---|---|---|---|---|---|
| | Peripheral | Central | Vertical | Number of defecation | Total |
| Control n = 16 | 17.4 ± 3.2 | 0.2 ± 0.2 | — | 0.5 ± 0.3 | 17.6 ± 3.4 |
| 0.1 n = 8 | 3.3 ± 1.1 ** | — | — | 3.0 ± 0.7 | 3.3 ± 1.1 *** |
| 1.C n = 8 | 5.3 ± 0.7 ** | — | — | — | 5.3 ± 0.7 ** |
| 5.0 n = 8 | 7.0 ± 2.8 * | — | — | 0.5 ± 0.5 | 7.0 ± 2.8 * |

Look the note in Tab. 1.

TABLE 3

The effect of the compound XVII on the behavior of Balb/c mice in "open-field" test (M ± $m_x$)

| Doses (mg/kg) | Types of activity | | | | |
|---|---|---|---|---|---|
| | Peripheral | Central | Vertical | Number of defecation | Total |
| Control n = 16 | 17.8 ± 3.8 | 0.2 ± 0.2 | — | 0.5 ± 0.1 | 18.0 ± 4.0 |
| 0.1 n = 8 | 4.0 ± 1.0 ** | 0.5 ± 0.5 | — | 2.0 ± 0.8 | 4.5 ± 1.5 ** |
| 1.0 n = 8 | 7.7 ± 1.9 * | — | — | 0.1 ± 0.1 | 7.7 ± i.9 * |

Look the note in Tab. 1.

TABLE 4

The effect of the compound XIX on the behavior of Balb/c mice in "open field" test (M ± $m_x$).

| Doses (mg/kg) | Types of activity | | | | |
|---|---|---|---|---|---|
| | Peripheral | Central | Vertical | Numbers of defecation | Total |
| Control n = 8 | 8.8 ± 1.6 | — | — | 1.0 ± 0.7 | 8.8 ± 1.6 |
| 0.1 n = 8 | 2.7 ± 1.0 ** | 0.3 ± 0.3 | — | 0.4 ± 0.4 | 3.0 ± 1.3 ** |
| 1.0 n = 8 | 3.1 ± 0.9 ** | 0.4 ± 0.4 | 0.1 ± 0.1 | 0.9 ± 0.6 | 3.6 ± 1.4 ** |
| 10.0 n = 8 | 1.8 ± 0.5 *** | — | — | 0.5 ± 0.5 | 1.8 ± 0.5 *** |

Look the note in Tab. 1

TABLE 5

The effect of the compound III on the behavior of Balb/c in "open-field" test (M ± $m_x$)

| Doses (mg/kg) | Types of activity | | | | |
|---|---|---|---|---|---|
| | Peripheral | Central | Vertical | Numbers of defecation | Total |
| Control n = 8 | 16.8 ± 2.7 | 1.8 ± 1.7 | — | 2.0 ± 0.8 | 18.8 ± 6.8 |
| 0.1 n = 8 | 28.1 ± 5.8 | 3.3 ± 2.0 | 0.6 ± 0.4 | 2.5 ± 0.9 | 32.1 ± 7.9 |
| 1.0 n = 8 | 35.8 ± 6.1 | 0.6 ± 0.3 | — | 2.5 ± 0.7 | 36.4 ± 6.4 |
| 5.0 n = 8 | 46.8 ± 9.9 * | 0.3 ± 0.3 | 0.4 ± 0.3 | 3.0 ± 0.7 | 47.5 ± 10.3 * |
| 10.0 n = 8 | 56.1 ± 12.2 * | 3.3 ± 2.1 | — | 2.0 ± 0.7 | 59.4 ± 13.8 * |
| 20.0 n = 8 | 24.0 ± 11.5 | — | — | 1.5 ± 0.7 | 24.1 ± 11.5 |

Look. the note in Tab. 1

TABLE 6

The effect of the compound III on the behavior of C57B1/6 mice in "open-field" test (M ± $m_x$).

| Doses (mg/kg) | Types of activity | | | |
|---|---|---|---|---|
| | Peripheral | Central | Vertical | Total |
| Control n = 8 | 109.8 ± 10.0 | 29.6 ± 6.4 | 21.9 ± 2.8 | 161.8 ± 11.3 |
| 0.1 n = 8 | 109.4 ± 8.3 | 42.1 ± 4.8 | 19.4 ± 3.4 | 170.9 ± 10.0 |

TABLE 6-continued

The effect of the compound III on the behavior of C57B1/6 mice in "open-field" test (M ± $m_x$).

| Doses | Types of activity | | | |
|---|---|---|---|---|
| (mg/kg) | Peripheral | Central | Vertical | Total |
| 0.5<br>n = 8 | 118.4 ± 9.0 | 42.1 ± 7.5 | 22.6 ± 2.0 | 184.6 ± 8.6 |
| 1.0<br>n = 8 | 107.8 ± 7.4 | 35.9 ± 7.6 | 22.3 ± 3.8 | 165.9 ± 13.5 |
| 5.0<br>n = 8 | 130.8 ± 16.8 | 28.8 ± 6.9 | 18.6 ± 2.7 | 177.8 ± 20.7 |
| 10.0<br>n = 8 | 118.0 ± 7.9 | 23.6 ± 5.3 | 12.9 ± 1.8 | 154.4 ± 13.3 |
| 50.0<br>n = 8 | 105.2 ± 11.9 | 24.0 ± 2.7 | 12.1 ± 1.3 | 141.3 ± 11.7 |

Look the note in Tab. 1

TABLE 7

The effect of the compound IV on the behavior of Balb/c mice in "open-field" test (M ± $m_x$)

| Doses<br>(mg/kg) | Types of activity | | | | |
|---|---|---|---|---|---|
| | Pepipheral | Central | Vertical | Numbers of defecation | Total |
| Control<br>n = 8 | 5.5 ± 0.8 | — | — | 1.5 ± 0.7 | 5.5 ± 0.8 |
| 0.1<br>n = 7 | 12.6 ± 2.6 * | — | — | 0.6 ± 0.5 | 12.6 ± 2.6 * |
| 1.0<br>n = 7 | 11.4 ± 2.3 * | — | — | — | 11.4 ± 2.3 * |
| 5.0<br>n = 7 | 13.6 ± 3.5 * | — | — | 1.7 ± 0.8 | 13.6 ± 3.5 * |
| 10.0<br>n = 8 | 9.5 ± 1.9 * | — | — | 3.0 ± 0.7 | 9.5 ± 1.9 * |
| 20.0<br>n = 8 | 8.9 ± 2.0 | — | — | 2.5 ± 0.7 | 8.9 ± 2.0 |

Look the note in Tab. 1

TABLE 8

The effect of the compound IV on the behavior of C57B1/6 mice in "open-field" test (M ± $m_x$)

| Doses<br>(mg/kg) | Types of activity | | | | |
|---|---|---|---|---|---|
| | Peripheral | Central | Vertical | Number of defecation | Total |
| Control<br>n = 8 | 64.1 ± 7.1 | 18.9 ± 2.9 | 10.8 ± 1.5 | 0.4 ± 0.2 | 93.8 ± 11.5 |
| 1.0<br>n = 8 | 62.8 ± 10.6 | 26.8 ± 4.9 | 9.3 ± 1.6 | 0.4 ± 0.2 | 99.3 ± 17.1 |
| 10.0<br>n = 8 | 52.8 ± 11.3 | 19.3 ± 4.5 | 11.1 ± 3.7 | 0.1 ± 0.1 | 83.2 ± 19.5 |

Look the note in Tab. 1

TABLE 9

The effect of the compound IX on the behavior of Balb/c mice in "open-field" test (M ± $m_x$)

| Doses<br>(mg/kg) | Types of activity | | | | |
|---|---|---|---|---|---|
| | Peripheral | Central | Vertical | Numbers of defecation | Total |
| Control<br>n = 18 | 19.4 ± 4.1 | — | — | 0.6 ± 0.6 | 19.9 ± 4.1 |
| 0.1<br>n = 8 | 15.1 ± 9.0 | — | — | 0.1 ± 0.1 | 15.1 ± 9.0 |
| 1.0<br>n = 8 | 39.8 ± 7.3 * | — | — | — | 39.8 ± 7.3 * |
| 5.0<br>n = 8 | 44.1 ± 10.2 * | — | — | — | 44.1 ± 10.2 * |
| 10.0<br>n = 8 | 36.8 ± 5.0 * | — | — | — | 36.8 ± 5.0 * |
| 20.0<br>n = 8 | 17.8 ± 5.5 | — | — | — | 17.8 ± 5.5 |

Look the note in Tab. 1

TABLE 10

The effect of the compound IX on the behavior of C57B1/6 mice in "open-field" test (M ± $m_x$)

| Doses<br>(mg/kg) | Types of activity | | | | |
|---|---|---|---|---|---|
| | Peripheral | Central | Vertical | Numbers of defecation | Total |
| Control<br>n = 8 | 86.3 ± 10.7 | 41.6 ± 10.0 | 11.4 ± 2.9 | 2.0 ± 0.8 | 139.3 ± 19.6 |
| 1.0<br>n = 8 | 70.9 ± 26.0 | 26.5 ± 4.3 | 8.1 ± 1.6 | 1.0 ± 0.7 | 106.8 ± 6.6 |
| 5.0<br>n = 8 | 78.8 ± 14.5 | 34.3 ± 12.9 | 10.8 ± 3.2 | 0.5 ± 0.5 | 125.0 ± 21.9 |

TABLE 10-continued

The effect of the compound IX on the behavior of C57B1/6 mice in "open-field" test (M ± m$_x$)

| Doses (mg/kg) | Types of activity | | | | |
|---|---|---|---|---|---|
| | Peripheral | Central | Vertical | Numbers of defecation | Total |
| 10.0 n = 8 | 70.6 ± 10.8 | 24.6 ± 8.2 | 11.3 ± 2.9 | 1.0 ± 0.7 | 106.6 ± 18.5 |

Look the note in Tab. 1

TABLE 11

The effect of the compound XII on the behavior of Balb/c in "open-field" test (M ± m$_x$)

| Doses (mg/kg) | Peripheral | Central | Vertical | Numbers of defecation | Total |
|---|---|---|---|---|---|
| Control n = 42 | 20.6 ± 1.9 | 0.3 ± 0.2 | 0.1 ± 0.1 | 1.5 ± 0.3 | 21.0 ± 2.2 |
| 0.001 n = 10 | 28.9 ± 8.8 | 1.6 ± 1.6 | — | — | 30.3 ± 9.4 |
| 0.01 n = 9 | 79.8 ± 9.3 *** | 2.6 ± 1.4 | 0.9 ± 0.6 | 3.1 ± 0.6 * | 83.2 ± 11.3 *** |
| 0.05 n = 8 | 37.1 ± 6.7 * | — | — | 2.0 ± 0.8 | 37.1 ± 6.7 * |
| 0.1 n = 10 | 70.6 ± 10.6 *** | 3.1 ± 2..1 * | — | 2.4 ± 0.7 | 73.7 ± 12.7 *** |
| 0.5 n = 10 | 77.6 ± 14.2 *** | 2.9 ± 1.5 | — | 1.6 ± 0.8 | 80.5 ± 15.7 ** |
| 1.0 n = 10 | 66.3 ± 11.1 *** | 0.5 ± 0.3 | — | 2.8 ± 0.9 | 68.8 ± 11.4 *** |
| 5.0 n = 10 | 43.0 ± 4.4 *** | 2.3 ± 1.5 | — | 0.8 ± 0.5 | 45.3 ± 5.9 * |
| 10.0 n = 10 | 54.8 ± 8.3 *** | 0.9 ± 0.3 | — | 2.0 ± 0.7 | 55.7 ± 8.6 *** |
| 30.0 n = 8 | 50.5 ± 7.9 *** | 1.1 ± 0.7 | 0.1 ± 0.1 | 4.5 ± 1.4 | 51.7 ± 8.7 *** |
| 50.0 n = 14 | 11.0 ± 1.6 *** | — | — | 1.6 ± 0.5 | 11.0 ± 1.6 *** |

Look the note in Tab. 1

TABLE 12

The effect of the compound XII on the behavior of C57B1/6 in "open-field" test (M ± m$_x$).

| Doses (mg/kg) | Types of activities | | | | |
|---|---|---|---|---|---|
| | Pepiferal | Central | Vertical | Numbers of defecations | Total |
| Control n = 17 | 85.1 ± 4.3 | 23.6 ± 4.8 | 18.8 ± 2.6 | 2.0 ± 0.8 | 127.5 ± 11.7 |
| 0.1 n = 8 | 92.9 ± 5.4 | 18.3 ± 1.9 | 12.5 ± 1.1 | 1.3 ± 0.3 | 123.6 ± 8.4 |
| 1.0 n = 8 | 86.6 ± 4.3 | 20.4 ± 2.3 | 16.5 ± 1.8 | 0.5 ± 0.5 | 123.5 ± 8.4 |
| 10.0 n = 8 | 86.6 ± 10.9 | 36.0 ± 4.9 | 17.6 ± 3.2 | 0.6 ± 0.6 | 140.2 ± 19.0 |
| 20.0 n = 8 | 86.4 ± 4.0 | 23.4 ± 4.9 | 17.4 ± 2.7 | 1.8 ± 0.6 | 127.2 ± 11.6 |
| 30.0 n = 8 | 53.0 ± 5.7 *** | 26.3 ± 10.2 | 8.3 ± 4.6 ** | 0.1 ± 0.1 * | 87.9 ± 17.5 * |
| 50.0 n = 8 | 67.1 ± 11.9 | 13.9 ± 5.3 | 9.1 ± 2.6 * | 0.5 ± 0.3 | 90.1 ± 19.8 |

Look the note to Tab. 1

TABLE 13

The effect of the compound XIII on the behavior of Balb/c mice in "open-field" test (M ± $m_x$)

| Doses (mg/kg) | Types of activity | | | | |
|---|---|---|---|---|---|
| | Pepipheral | Central | Vertical | Numbers of defecation | Total |
| Control n = 10 | 20.8 ± 5.2 | 2.1 ± 1.6 | — | 1.6 ± 1.0 | 22.9 ± 6.8 |
| 0.5 n = 10 | 32.0 ± 5.7 | 4.3 ± 4.1 | — | 2.9 ± 0.6 | 36.3 ± 9.8 |
| 1.0 n = 10 | 80.0 ± 11.2 ** | 0.8 ± 0.5 | — | 1.0 ± 0.5 | 80.8 ± 11.7 ** |
| 5.0 n = 10 | 69.0 ± 13.2 ** | — | — | 1.6 ± 0.7 | 69.0 ± 13.2 ** |
| 50.0 n = 10 | 27.7 ± 6.2 | 0.7 ± 0.5 | — | — | 28.4 ± 6.7 |

Look the note in Tab. 1

TABLE 14

The effect of the compound XIII on the behavior of C57B1/6 in "open-field" test (M ± $m_x$)

| Doses (mg/kg) | Types of activity | | | |
|---|---|---|---|---|
| | Peripheral | Central | Vertical | Total |
| Control n = 8 | 79.8 ± 9.9 | 33.3 ± 6.3 | 16.3 ± 2.6 | 129.4 ± 18.8 |
| 1.0 n = 8 | 79.6 ± 5.3 | 37.6 ± 7.9 | 14.8 ± 2.7 | 132.0 ± 15.9 |
| 10.0 n = 8 | 84.1 ± 9.9 | 22.4 ± 3.5 | 12.9 ± 3.5 | 119.4 ± 16.4 |
| 50.0 n = 8 | 63.3 ± 8.4 | 20.0 ± 5.3 | 11.8 ± 3.0 | 95.1 ± 16.7 |

Look the note in Tab. 1

TABLE 15

The effect of the compound XIV on the behavior of Balb/c mice in "open field" test (M ± $m_x$)

| Doses (mg/kg) | Types of activity | | | | |
|---|---|---|---|---|---|
| | Peripheral | Central | Vertical | Numbers of defecation | Total |
| Control n = 23 | 20.0 ± 2.7 | 0.7 ± 0.4 | 0.2 ± 0.1 | 1.5 ± 0.3 | 20.9 ± 3.2 |
| 0.1 n = 14 | 27.0 ± 6.3 * | 1.1 ± 0.7 | 0.1 ± 0.1 | 1.3 ± 0.5 | 28.2 ± 7.1 |
| 0.5 n = 14 | 44.4 ± 9.2 * | 4.7 ± 2.7 | 0.3 ± 0.3 | 1.0 ± 0.4 | 49.4 ± 10.7 * |
| 1.0 n = 14 | 38.7 ± 4.8 ** | 0.9 ± 0.8 | 0.1 ± 0.1 | 2.9 ± 0.7 | 39.7 ± 5.7 ** |
| 5.0 n = 6 | 58.7 ± 7.2 *** | 2.8 ± 1.8 | — | 0.7 ± 0.7 | 61.3 ± 9.0 *** |
| 10.0 n = 6 | 67.8 ± 11.1 *** | — | — | 2.0 ± 0.9 | 67.8 ± 11.1 *** |
| 20.0 n = 8 | 17.3 ± 8.0 | 3.4 ± 3.4 | 0.1 ± 0.1 | 0.1 ± 0.1 | 20.8 ± 9.6 |

Look the note in Tab. 1

TABLE 16

The effect of the compound XIV on the behavior of C57B1/6 in "open-field" test (M ± $m_x$)

| Doses (mg/kg) | Types of activity | | | |
|---|---|---|---|---|
| | Peripheral | Central | Vertical | Total |
| Control n = 8 | 72.1 ± 9.0 | 30.5 ± 7.2 | 13.5 ± 2.3 | 116.1 ± 18.5 |
| 0.5 n = 8 | 78.4 ± 9.8 | 24.8 ± 4.6 | 11.0 ± 2.9 | 114.2 ± 17.3 |
| 5.0 n = 8 | 69.5 ± 11.3 | 37.1 ± 4.7 | 12.5 ± 2.1 | 119.1 ± 18.1 |
| 10.0 n = 8 | 79.0 ± 6.8 | 35.1 ± 5.0 | 15.3 ± 3.2 | 129.4 ± 15.0 |

Look the note in Tab. 1

TABLE 17

The effect of the compound XV on the behavior of Balb/c in "open-field" test (M ± $m_x$).

| Doses (mg/kg) | Periphepal | Central | Vertical | Numbers of defecation | Total |
|---|---|---|---|---|---|
| Control n = 11 | 17.6 ± 2.7 | 1.9 ± 1.5 | — | 1.8 ± 0.9 | 19.5 ± 4.2 |
| 0.5 n = 10 | 32.1 ± 4.7 * | 0.5 ± 0.4 | — | 1.6 ± 0.7 | 32.6 ± 5.0 * |
| 1.0 n = 10 | 37.7 ± 5.5 | 5.1 ± 4.4 ** | — | 2.0 ± 0.9 | 42.8 ± 9.9 |
| 5.0 n = 10 | 39.1 ± 8.6 * | — | — | 3.6 ± 0.9 | 39.1 ± 8.6 * |
| 75.0 n = 6 | 8.8 ± 2.9 * | — | — | 2.7 ± 1.3 | 8.8 ± 2.9 * |
| 100.0 n = 6 | 6.5 ± 3.1 * | — | — | — | 6.5 ± 3.1 * |
| Control n = 8 | 13.8 ± 5.4 | — | — | 2.0 ± 0.8 | 13.8 ± 5.4 |
| 0.01 n = 8 | 6.9 ± 1.8 | — | — | 0.5 ± 0.5 | 6.9 ± 1.8 |
| 0.1 n = 8 | 11.1 ± 2.1 | — | — | 1.0 ± 0.7 | 11.2 ± 2.1 |
| 10.0 n = 8 | 44.9 ± 13.0 * | 0.6 ± 0.5 | 0.4 ± 0.3 | — | 45.9 ± 13.8 * |

Look the note in Tab. 1

TABLE 18

The effect of the compound XV on the behavior of C57B1/6 mice in "open-field" test (M ± $m_x$)

| Doses (mg/kg) | Pepipheral | Central | Vertical | Total |
|---|---|---|---|---|
| Control n = 8 | 69.9 ± 4.5 | 33.6 ± 6.2 | 12.3 ± 0.9 | 415.8 ± 11.6 |
| 1.0 n = 8 | 87.8 ± 6.7 | 39.0 ± 6.9 | 11.4 ± 2.5 | 138.2 ± 16.1 |
| 5.0 n = 8 | 87.8 ± 14.6 | 36.4 ± 5.7 | 14.9 ± 2.3 | 139.1 ± 22.6 |
| 50.0 n = 8 | 54.1 ± 10.7 | 35.0 ± 8.1 | 6.3 ± 1.6 | 95.4 ± 20.4 |

Look the note in Tab. 1

TABLE 19

The effect of the compounds IV, XII, XIV N XV on the the behavior of rats in conflict Vogel test (M ± $m_x$).

| Doses (mg/kg) | XII | IV | XV | XIV |
|---|---|---|---|---|
| Control | 8.3 ± 1.5 n = 12 | 14.5 ± 3.0 n = 13 | 14.5 ± 3.0 n = 13 | 14.5 ± 3.0 n = 13 |
| 1.0 | 15.3 ± 3.4 n = 8 * | 29.7 ± 5.3 n = 6 * | 59.1 ± 16.7 n = 8 * | 31.6 ± 7.6 n = 8 * |
| 5.0 | 19.0 ± 2.5 n = 11 ** | 31.0 ± 5.6 n = 6 * | 35.3 ± 5.5 n = 8 ** | 32.9 ± 5.8 n = 10 * |
| 10.0 | 15.4 ± 2.5 n = 11 * | 35.8 ± 7.8 n = 6 * | 38.0 ± 9.4 fl = 5 * | 36.0 ± 9.4 n = 10 * |

TABLE 19-continued

The effect of the compounds IV, XII, XIV N XV on the the behavior of rats in conflict Vogel test (M ± $m_x$).

| Doses (mg/kg) | XII | IV | XV | XIV |
|---|---|---|---|---|
| 20.0 | 28.0 ± 5.8 n = 12 ** | 62.3 ± 19.5 n = 6 * | 73.9 ± 24.1 n = 10 * | 42.3 ± 10.8 n = 12 * |

Look the note in Tab. 1

TABLE 20

The effects of the compounds IV, XII, XIV N XV on the time of remaining on the rotarod (sec) (M ± $m_x$)

| Doses (mg/kg) | XII | IV | XV | XIV |
|---|---|---|---|---|
| Control | 120.0 + 0 n = 16 | 120 + 0 n = 8 | 120 + 0 n = 8 | 120 + 0 n = 8 |
| 0.01 | 120.0 + 0 n = 12 | — | — | — |
| 0.1 | 120.0 + 0 n = 12 | 120 + 0 n = 8 | 120 + 0 n = 8 | 120 + 0 n = 8 |
| 1.0 | 120.0 + 0 n = 12 | 120 + 0 n = 8 | 120 + 0 n = 8 | 120 + 0 n = 8 |
| 5.0 | 120.0 + 0 n = 12 | 120 + 0 n = 8 | 120 + 0 n = 8 | 120 + 0 n = 8 |
| 10.0 | 120.0 + 0 n = 12 | 120 + 0 n = 8 | 120 + 0 n = 8 | 120 + 0 n = 8 |
| 20.0 | 118.8 + 1.6 n = 12 | 120 + 0 n = 8 | 120 + 0 n = 8 | 120 + 0 n = 8 |
| 50.0 | 111.3 + 7.5 n = 12 | — | — | — |

Look the note in Tab. 1

TABLE 21

The effect of the compounds IV, XII, XIV N XV on the latent time of sleep (sec) in mice after administration of sodium thiopental (M ± $m_x$)

| Doses (mg/kg) | Compounds | | | |
|---|---|---|---|---|
| | XII | IV | XV | XIV |
| Control | 1.89 + 0.19 | 2.4 + 0.2 | 2.6 + 0.3 | 2.6 + 0.4 |
| | n = 18 | n = 8 | n = 8 | n = 8 |
| 0.01 | 1.86 + 0.27 | — | — | — |
| | n = 8 | | | |
| 0.1 | 1.94 + 0.18 | — | — | — |
| | n = 8 | | | |
| 0.5 | — | 3.0 + 0.3 | 2.5 + 0.2 | 2.5 + 0.5 |
| | | n = 8 | n = 8 | n = 8 |
| 1.0 | 2.78 + 0.17 | 2.7 + 0.3 | 2.8 + 0.2 | 2.5 + 0.2 |
| | n = 9 | n = 8 | n = 8 | n = 8 |
| 5.0 | 2.21 + 0.17 | 2.8 + 0.3 | 2.3 + 0.2 | 2.2 + 0.2 |
| | n = 9 | n = 8 | n = 8 | n = 7 |
| 10.0 | 2.28 + 0.24 | 2.5 + 0.1 | 2.8 + 0.3 | 2.9 + 0.4 |
| | n = 9 | n = 8 | n = 8 | n = 6 |

Look the note in Tab. 1

TABLE 22

The effect of the compounds IV, XII, XIV N XV on the duration of sleep (min) in mice after administration of sodium thiopental (M ± $m_x$)

| Doses (mg/kg) | Compounds | | | |
|---|---|---|---|---|
| | XII | IV | XV | XIV |
| Control | 102.9 ± 14.9 | 67.7 ± 15.7 | 76.0 ± 14.6 | 119.5 ± 17.4 |
| | n = 18 | n = 8 | n = 8 | n = 8 |
| 0.01 | 76.4 ± 16.7 | — | — | — |
| | n = 8 | | | |
| 0.1 | 54.5 ± 9.9 | — | — | — |
| | n = 8 | | | |
| | * | | | |
| 0.5 | — | 42.8 ± 13.5 | 78.4 ± 18.2 | 91.0 ± 17.8 |
| | | n = 8 | n = 8 | n = 8 |
| 1.0 | 67.9 ± 4.3 | 32.5 ± 7.9 | 70.5 ± 13.7 | 69.S ± 15.8 |
| | n = 9 | n = 8 | n = 8 | n = 8 |
| | * | | | * |
| 5.0 | 71.7 ± 14.6 | 50.7 ± 11.0 | 56.8 ± 19.1 | 86.4 ± 13.9 |
| | n = 9 | n = 8 | n = 8 | n = 7 |
| 10.0 | 92.4 ± 9.9 | 45.1 ± 10.6 | 74.7 ± 18.7 | 70.6 ± 9.0 |
| | n = 9 | n = 8 | n = 8 | n = 6 |
| | | | | * |

Look the note in Tab. 1

TABLE 23

The effect of the compound VIII at dose of 1.0 mg/kg (i.v.) on the hemodynamics and intact heart activity in cats (n = 5. M ± m)

| Parameter | The changes after drug injection, % from basal level | | | | | |
|---|---|---|---|---|---|---|
| | after injection | after 2 min | after 5 min | after 10 min | after 20 min | after 30 min |
| Mean blood pressure | −14.8 ± 12.5 | −1.8 ± 3.8 | −2.8 ± 5.7 | −7.8 ± 5.7 | −12.0 ± 5.0 | −6.5 ± 5.7 |
| Heart rate | −15.3 ± 1.1** | −10.9 ± 2.3* | −3.2 ± 1.4 | −4.4 ± 1.9 | −3.2 ± 1.8 | −5.4 ± 3.1 |
| Stroke volume | 63.2 ± 14.0* | +20.6 ± 6.5* | +5.6 ± 10.8 | −3.5 ± 8.7 | −4.5 ± 8.4 | +3.5 ± 3.5 |
| Cardiac volume | 38.1 ± 11.6* | +7.0 ± 2.9 | +6.0 ± 12.8 | −7.5 ± 9.6 | −7.2 ± 9.2 | −2.2 ± 3.0 |
| Aortic blood flow accelaration | +31.3 ± 10.8 | +3.3 ± 2.7 | −2.0 ± 9.0 | −5.2 ± 7.8 | −6.2 ± 7.6 | +1.2 ± 2.1 |

\* - $p < 0.05$
\*\* - $p < 0.01$ in comparison to basal level

TABLE 24

The effect of the compound IX on the hemodynainics and intact heart activity in cats (n = 7, M ± m)

| Parameter | Dose mg/kg | The changes after drug injection, % from basal level | | | | | |
|---|---|---|---|---|---|---|---|
| | | after injection | after 2 min | after 5 min | after 10 min | after 20 min | after 30 min |
| Mean blood pressure | 0.5 | −2.1 ± 3.0 | +4.4 ± 4.7 | −5.4 ± 2.3 | −1.2 ± 3.6 | −4.1 ± 4.8 | −4.9 ± 6.5 |
| | 1.0 | −1.6 ± 7.3 | +0.6 ± 2.7 | −3.8 ± 3.4 | −6.8 ± 2.5* | −1.9 ± 2.9 | −2.7 ± 2.9 |
| Heart rate | 0.5 | −8.0 ± 3.5 | −11.6 ± 2.8** | −91 ± 2.5* | −7.3 ± 1.6** | −4.5 ± 2.2 | −5.3 ± 2.3 |
| | 1.0 | −15.4 ± 2.7** | −14.1 ± 2.1** | −10.6 ± 1.5** | −7.1 ± 1.0** | −4.2 ± 1.9 | −2.3 ± 3.5 |
| Stroke volume | 0.5 | +17.0 ± 5.5* | +9.4 ± 6.5 | +5.6 ± 5.6 | +3.6 ± 3.0 | −0.7 ± 4.0 | +1.8 ± 9.3 |
| | 1.0 | +34.21 ± 0.6* | +19.3 ± 4.6** | +13.8 ± 7.8 | +5.9 ± 6.3 | +4.4 ± 4.5 | +0.7 ± 6.7 |

TABLE 24-continued

The effect of the compound IX on the hemodynainics and intact heart activity in cats
(n = 7, M ± m)

| | | The changes after drug injection, % from basal level | | | | | |
|---|---|---|---|---|---|---|---|
| Parameter | Dose mg/kg | after injection | after 2 min | after 5 min | after 10 min | after 20 min | after 30 min |
| Cardiac volume | 0.5 | +6.5 ± 2.8 | −3.5 ± 6.0 | −1.7 ± 4.8 | −4.2± 2.1 | −6.1 ± 3.4 | −2.8 ± 7.8 |
| | 1.0 | +17.6 ± 8.2 | +2.2 ± 3.5 | +1.7 ± 6.8 | −1.3 ± 6.8 | −0.2 ± 3.8 | −2.5 ± 5.1 |
| Mean blood flow accelaration | 0.5 | +8.8 ± 5.8 | +11.0 ± 8.8 | +0.6 ± 4.9 | +3.0 ± 4.0 | +5.6 ± 5.1 | +1.8 ± 5.8 |
| | 1.0 | +14.8 ± 8.8 | ± 8.6 +3.8 | +13.6 ± 5.7 | +9.6 ± 3.9* | +13.1 ± 5.0* | +3.9 ± 2.0 |

\* - p < 0.05
\*\* - p < 0.01 in comparison to basal level

TABLE 25

The effect of the compound XX on the hemodynamics and intact heart activity in cats
(n = 5, M ± m)

| | | The changes after drug injection, % from basal level | | | | | |
|---|---|---|---|---|---|---|---|
| Parameter | Dose mg/kg | after injection | after 2 min | after 5 min | after 10 min | after 20 min | after 30 min |
| Mean blood pressure | 1.0 | −0.9 ± 2.7 | ± 5.1 ± 1.7* | +2.0 ± 1.0 | +1.7 ± 1.2 | +3.3 ± 2.4 | +0.3 ± 3.0 |
| | 2.0 | −13.6 ± 5.1 | ± 4.6 ± 3.5 | +3.3 ± 2.5 | −1.0 ± 1.8 | −5.3 ± 0.8** | −9.6 ± 3.5 |
| Heart rate | 1.0 | −7.9 ± 1.7** | −4.9 ± 1.5* | −5.2 ± 2.1 | −4.3 ± 1.9 | −5.0 ± 4.2 | −5.0 ± 4.2 |
| | 2.0 | −10.7 ± 2.5* | −5.2 ± 1.8* | −4.5 ± 1.4* | −3.1 ± 1.6 | −3.6 ± 1.7 | −4.0 ± 2.2 |
| Stroke volume | 1.0 | +25.2 ± 2.6** | +7.9 ± 1.6** | +1.7 ± 3.4 | +0.6 ± 3.5 | +1.4 ± 3.8 | −0.5 ± 4.4 |
| | 2.0 | +38.5 ± 10.6* | +6.9 ± 3.1 | +4.2 ± 3.8 | +1.8 ± 2.1 | −1.1 ± 5.4 | +1.7 ± 3.9 |
| Cardiac volume | 1.0 | +15.1 ± 1.6** | +2.5 ± 0.9 | −3.9 ± 1.5 | −3.9 ± 2.8 | −4.1 ± 2.8 | −7.0 ± 3.4 |
| | 2.0 | +22.7 ± 6.6* | +1.2 ± 2.8 | −0.5 ± 3.1 | −1.4 ± 3.0 | −4.7 ± 5.2 | −5.5 ± 5.2 |
| Mean blood flow accelaration | 1.0 | +10.7 ± 3.3* | −1.4 +1.8 | −3.6 ± 2.4 | −0.6 ± 2.1 | −2.8 ± 2.6 | −3.2 ± 1.8 |
| | 2.0 | +22.5 ± 9.3 | −3.0 ± 3.9 | +1.6 ± 5.1 | −1.0 ± 3.1 | −3.8 ± 4.0 | −6.2 ± 4.9 |

\* - p < 0.05
\*\* - p < 0.01 in comparison to basal level

TABLE 26

The effect of the compound XXIII (1.0 mg/kg, i.v.) on the hemodynamycs and heart activity.

| | The changes in comparison to basal level, in %. M ± m, n = 7 Time after injection, min | | | | | |
|---|---|---|---|---|---|---|
| Parameter | 0.25 | 2 | 5 | 10 | 20 | 30 |
| Mean blood pressure | −13.9 ± 2.9** | −0.2 ± 4.0 | +3.4 ± 2.5 | +3.8 ± 3.2 | +2.8 ± 2.8 | +2.9 ± 3.2 |
| Heart rate | −14.6 ± 1.2** | −11.7 ± 1.3** | −7.9 ± 1.6** | −5.1 ± 1.2** | −3.8 ± 1.5* | −4.1 ± 1.0* |
| Cardiac volume | +3.6 ± 3.5 | −3.6 ± 2.0 | −0.6 ± 2.3 | −0.7 ± 3.6 | −4.2 ± 2.4 | −4.5 ± 3.5 |
| Mean blood flow accelaration | +2.1 ± 4.9 | −4.9 ± 4.7 | −1.0 ± 5.0 | +8.1 ± 3.0* | +4.3 ± 2.7 | −2.4 ± 3.4 |

\* p<0.05
\*\* p<0.01 in comparison to basal level

TABLE 27

The effect of the verapamil (0.5 mg/kg, i.v.) on the hemodynamics and heart activity The changes in comparison to basal level, in %, M ± m, n = 7
Time after injection, min

| Parameter | 0.25 | 2 | 5 | 10 | 20 | 30 |
|---|---|---|---|---|---|---|
| Mean blood pressure | −40.4 ± 7.0** | −22.7 ± 8.1 | −8.7 ± 6.3 | −2.4 ± 2.6 | −8.5 ± 6.6 | −11.6 ± 7.0 |
| Heart rate | −13.7 ± 1.7** | −11.8 ± 2.0** | −12.3 ± 3.0** | −8.1 ± 2.0** | −5.4 ± 2.0* | −4.6 ± 3.4 |
| Cardiac volume | −12.3 ± 4.5* | +7.5 ± 6.8 | +4.4 ± 4.7 | −0.3 ± 1.8 | −9.5 ± 2.3** | −7.2 ± 6.0 |
| Mean blood flow accelaration | −32.5 ± 5.7** | −15.5 ± 2.4** | −8.1 ± 3.0* | −9.9 ± 2.5** | −8.7 ± 3.0 | −7.0 ± 4.2 |

* $p<0.05$
** $p<0.01$ in comparison to basal level

TABLE 28

The effect of the compound VIII (1.0 mg/kg, i.v.) on the mean elevation of ST-segment in epicardium electrogram during 5-min occlusion with following reperfusion of coronary artery in anesthized cats (n = 6)

The changes in the elevation of ST-segment in comparison to control occlusion (probability interval, mv)

| | 30 sec of occlusion | 1 min of occlusion | 2 min of occlusion | 4 min of occlusion | 5 min of occlusion | 15 sec of reperfusionl |
|---|---|---|---|---|---|---|
| Occlusion immediately after injection | −1.20* −1.80−−0.50 | −0.90* −1.60−−0.40 | −1.25* −3.00−−0.30 | −0.70 −1.40−±0.30 | −0.80 −1.40−0 | −0.40 −0.70−−0.10 |
| Occlusion 20 min after injection | −0.45 −1.00−+0.05 | −0.30 −1.10−+0.60 | −0.50 −2.05−+0.20 | −0.50 −1.00−+0.50 | −0.25 −0.80−+1.0 | −0.80−+0.20 |
| Occlusion 40 min after injection | −0.55 −1.20−+0.1 | −0.35 −1.35−+0.65 | −0.40 −2.00−+0.60 | −0.50 −1.45−+0.70 | −0.85 −1.90−+0.50 | −0.75 −1.15−0 |

* - $p < 0.05$ in comparison to control occlusion

TABLE 29

The effect of the compound IX (1.0 mg/kg. i.v.) on the mean elevation of ST-segment in epicardium electrogram during 5-min occlusion with following reperfusion of coronary artery in anethetized cats (n = 6)

The changes in the elevation of ST-segment in comparison to control occlusion (probability interval, my)

| | 30 sec of occlusion | 1 min of occlusion | 2 min of occlusion | 3 min of occlusion | 5 min of occlusion | 15 sec of reperfusion |
|---|---|---|---|---|---|---|
| Occlusion immediately after injection | −1.8** −3.1÷−1.4 | −1.9** −2.9÷−0.8 | −2.4** −3.7÷−1.0 | −1.9** −5.8÷−1.0 | −2.2** −6.5÷−0.4 | −1.2* −2.3÷−0.2 |
| Occlusion 20 min after injection | −0.7 −2.0÷ 0.0 | −.0.7 −1.0÷+0.1 | −1.4* −2.7÷−0.5 | −1.4* −2.7÷−0.2 | −1.2 −3.0÷±0.6 | −0.8* −1.5÷−0.1 |
| Occlusion 40 min after injection | −0.5 −1.1 ÷ 0.0 | −0.5* −1.65÷−0.1 | −1.0* −2.4÷−0.2 | −1.2 −3.8÷+ 0.6 | −1.0 −3.0÷+ 1.0 | −1.0* −1.9÷−0.2 |

* - $p < 0.05$
** - $p < 0.01$ in comparison to control level

TABLE 30

The anti-arrhythmic activity of the compounds IX and XX

| Compounds | Adrenaline arrhythmia. Range of active doses mg/kg | Calcium chloride arrhythmia ED50, mg/kg | Aconitine arrhythmia ED50, mg/kg | Acute toxicity LD50, mg/kg | LD50/ED50 |
|---|---|---|---|---|---|
| Compound XX | 0.2–0.7 | 2.0 1.7–2.4 | <0.5 | no data | no data |
| Compound IX | 0.3–0.7 | 1.0 0.7–1.3 | 1.2 0.9–1.5 | 31.5 31.4–31.6 | 26.2 |
| Novocainamide | — | 50.0 | 41 | 110.0 | 2.7 |
| Lidocaine | 5.0-8.0 | 7.5 | 7.8 | 39.4 | 5.0 |
| Bonnecor | | 1.6 | 0.23 | 11.5 | 50 |
| Etmosin | | | 0.28 | 16.4 | 58.6 |
| Verapamil | 0.3–1.0 | 1.1 | — | 17.0 | |
| Propranolol | 0.3–1.0 | 0.8 | — | 9.6 | |

TABLE 31

The effect of the compounds IX, XX and bonnecor on the incidence of ventricular fibrillations and lethality hazardous arrhythmia during 7-min occlusion with following reperfusion of coronary artery.

| Compound | Number of animals | Number of VF | Number of LHA | Total numbers of arrhyt. | Severity of arrhythmias (in points) |
|---|---|---|---|---|---|
| Control | 24 | 15 | 22 | 24 | 66 |
| Bonnecor 1, 0 mg/kg | 18 | 6* | 12* | 16 | 36* |
| Compound IX 2 mg/kg | 20 | 4* | 12* | 17^ | 32** |
| Compound XX 1 mg/kg | 18 | 7^ | 11* | 13** | 34* |

^p ≦ 0, 1; *p ≦ 0, 05; **p ≦ 0, 01—in comparison to control
VF-ventricular fibrillations
LHA-lethality hazardous arrhythmia (VF + paroxysmal ventricular tachycardia)

TABLE 32

The effect of the compound IX at dose of 2 mg/kg (i.v.) on the ventricular disterbances of heart rhythm in concious dogs (n = 5, M ± m ).

| | The changes in comparison to basal level after compound injection | | | | | |
|---|---|---|---|---|---|---|
| Parameter | after 3 min | after 5 min | after 10 min | after 20 min | after 30 min | after 60 min |
| Heart, rate beats/min | +3.2 ± 8.4 | −5.2 ± 9.2 | −14.6 ± 12.0 | −16.4 ± 6.6 & | −5.6 ± 2.1 & | −5.2 ± 4.1 & |
| % ectopic contractions | −44.8 ± 15.0* | −43.8 ± 13.3* | −59.4 ± 7.8** | −41.4 ± 8.1** | −24.8 ± 5.8* | −17.2 ± 9.1 |

*p < 0.05
**p < 0.01 in comparison to basal level
& - p < 0.1

TABLE 33

The effect of the compound XXIII at dose of 2 mg/kg (i.v.) on the ventricular disterbances of heart rhythm in concious dogs (n = 5, M ± m ).

| Parameter | The changes in comparison to basal level after compound injection | | | | | | |
|---|---|---|---|---|---|---|---|
| | after 1 min | after 3 min | after 5 min | after 10 min | after 15 min | after 30 min | after 60 min |
| Heart rate beats/min | −19.0 ± 2.5** | −25,8 ± 455** | −30.4 ± 4.5** | −32.6 ± 359** | −29.0 ± 5.5** | −14.0 ± 4.8* | −12.0 ± 5.5* |
| % ectopic contractions | −57.4 ± 17.6* | −66.2 ± 18.1* | −54.6 ± 16.8* | −22.6 ± 8.9* | −24.8 ± 11.1* | −8.8 ± 4.7 | −5.2 ± 2.6 |

*$p < 0.05$
**$p < 0.01$ in compapison to basal level

TABLE 34

The effect of the compound XX (1.0 mg/kg. i.v.) on the heart rate (beats/min) and % of the ectopic contractions* in concious dogs according to Harris.

| Number of dog | basal level | Time after compound injection, min | | | | | | |
|---|---|---|---|---|---|---|---|---|
| | | 3 | 5 | 10 | 15 | 20 | 30 | 40 | 50 |
| 1 | 131/97 | 103/80 | 98/82 | 75/81 | 100/91 | 78/92 | 117/91 | 106/97 | 109/94 |
| 2 | 122/57 | 93/64 | 89/52 | 102/50 | 88/51 | 74/56 | 94/62 | 105/66 | 128/63 |
| 3 | 183/36 | 172/30 | 167/20 | 163/18 | 159/0 | 155/0 | 168/10 | 185/8 | 198/10 |
| 4 | 164/88 | 145/72 | 138/63 | 129/60 | 125/58 | 132/66 | 135/74 | 148/79 | 159/81 |

*heart rate / % of the ectopic contpactions

What is claimed is:

1. A compound of the formula

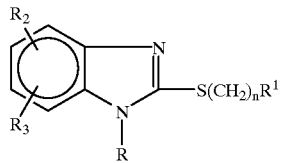

wherein n is 2, R is hydrogen, $R^1$ is selected from the group consisting of dimethylamino, diethylamino, piperidino, pyrrolidino, morpholino and 4-methylpiperazino, $R_2$ is ethoxy, and $R_3$ is hydrogen, or a pharmaceutically acceptable salt thereof.

2. A compound according to claim 1 wherein n=2, $R_1$=NMe$_2$, $R_2$=OEt, and $R_3$=H.

3. A compound according to claim 1 wherein n=2, $R_1$=NEt$_2$, $R_2$=OEt, and $R_3$=H.

4. A compound according to claim 1 wherein n=2, $R_1$=

$R_2$=OEt, and $R_3$=H.

* * * * *